US007351415B2

(12) United States Patent
Evans et al.

(10) Patent No.: US 7,351,415 B2
(45) Date of Patent: *Apr. 1, 2008

(54) ADENOVIRUS FORMULATIONS

(75) Inventors: Robert K. Evans, Souderton, PA (US); David B. Volkin, Doylestown, PA (US)

(73) Assignee: Merck & Co., Inc., Rahway, NJ (US)

( * ) Notice: Subject to any disclaimer, the term of this patent is extended or adjusted under 35 U.S.C. 154(b) by 460 days.

This patent is subject to a terminal disclaimer.

(21) Appl. No.: 10/791,503

(22) Filed: Mar. 2, 2004

(65) Prior Publication Data

US 2004/0166122 A1 Aug. 26, 2004

Related U.S. Application Data

(63) Continuation of application No. 09/799,937, filed on Mar. 6, 2001, now abandoned.

(60) Provisional application No. 60/187,440, filed on Mar. 7, 2000.

(51) Int. Cl.
*A61K 39/00* (2006.01)
*A61K 39/12* (2006.01)
*A61K 39/23* (2006.01)
*A61K 39/095* (2006.01)

(52) U.S. Cl. .............................. 424/233.1; 424/184.1; 424/204.1

(58) Field of Classification Search ...................... None
See application file for complete search history.

(56) References Cited

U.S. PATENT DOCUMENTS

| 5,932,223 | A | 8/1999 | Burke et al. |
| 6,039,958 | A | 3/2000 | Koyama et al. |
| 6,225,289 | B1 | 5/2001 | Kovesdi et al. |
| 6,514,943 | B2 | 2/2003 | Kovesdi et al. |
| 6,689,600 | B1 | 2/2004 | Wu et al. |
| 6,710,173 | B1 * | 3/2004 | Binley et al. ............. 536/23.72 |
| 6,730,328 | B2 | 5/2004 | Maskiewicz et al. |
| 2002/0031527 | A1 * | 3/2002 | Wu et al. ................. 424/233.1 |
| 2005/0186225 | A1 | 8/2005 | Evans et al. |

FOREIGN PATENT DOCUMENTS

WO WO 99/45841 9/1999

OTHER PUBLICATIONS

Evans et al., Evaluation of Degradation Pathways for Plasmid DNA in Pharmaceutical Formulations via Accelerated Stability Studies, 2000, Journal of Pharmaceutical Sciences, vol. 89, No. 1, pp. 76-87.*

* cited by examiner

*Primary Examiner*—Bruce R. Campell
(74) *Attorney, Agent, or Firm*—Henry P. Wu

(57) ABSTRACT

The invention relates to viral formulations and related pharmaceutical products for use in gene therapy and/or vaccine applications. Especially preferred viral formulations disclosed herein are liquid adenovirus formulations, which show improved stability when stored in about the 2-8° C. range while also being compatible with parenteral administration. These formulations comprise a buffer, a sugar, a salt, a divalent cation, a non-ionic detergent, as well as a free radical scavenger and/or a chelating agent to inhibit free radical oxidation.

37 Claims, 32 Drawing Sheets

Effect of oxidation inhibitors on the stability of Ad5gag in A105

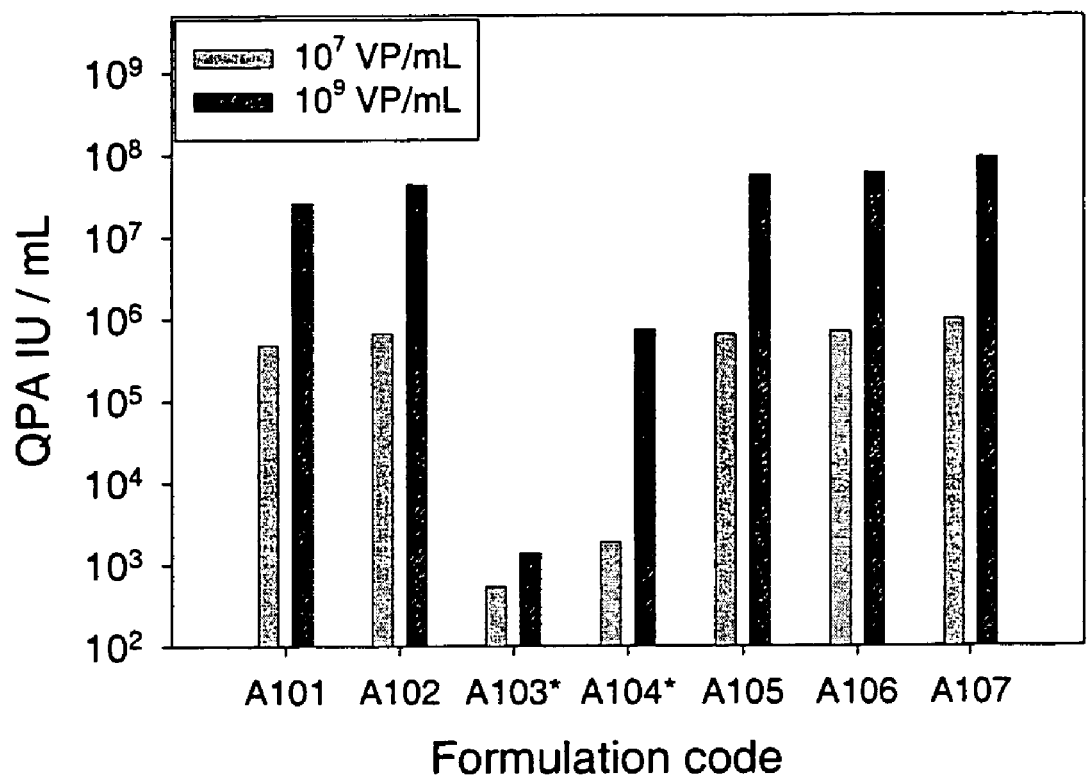
Figure 1. Effect of one freeze/thaw cycle on the stability of Ad5gag in candidate formulations
*QPA assays of these two formulations showed either little infection or wide margin of error.
Variability of assay ~ 0.15 logs.

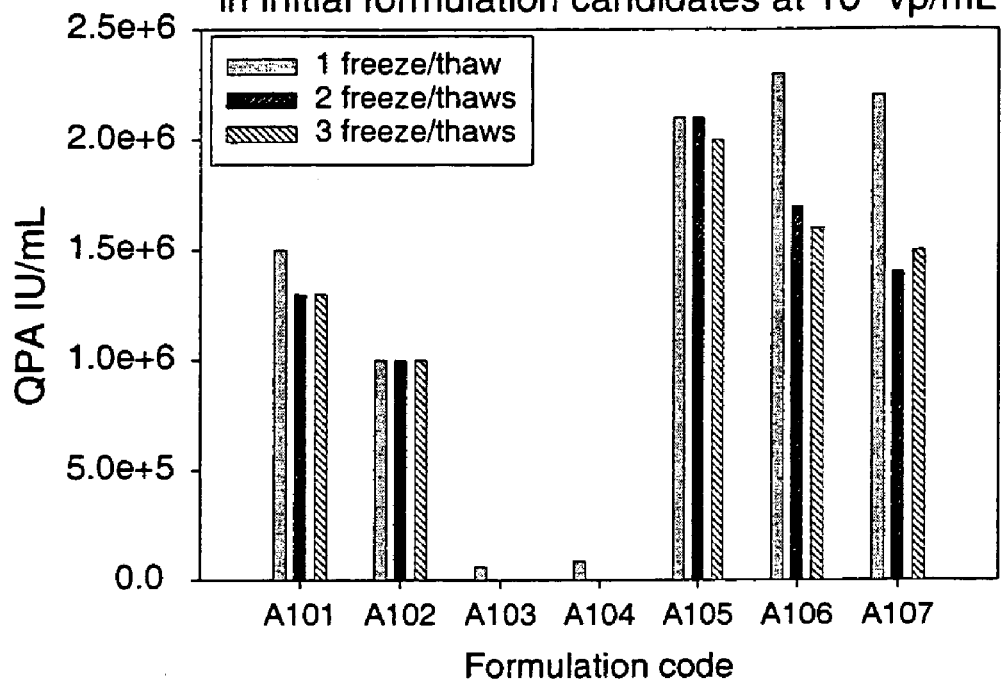
Figure 2. Effect of freeze/thaw on the stability of Ad5gag in initial formulation candidates at $10^7$ vp/mL

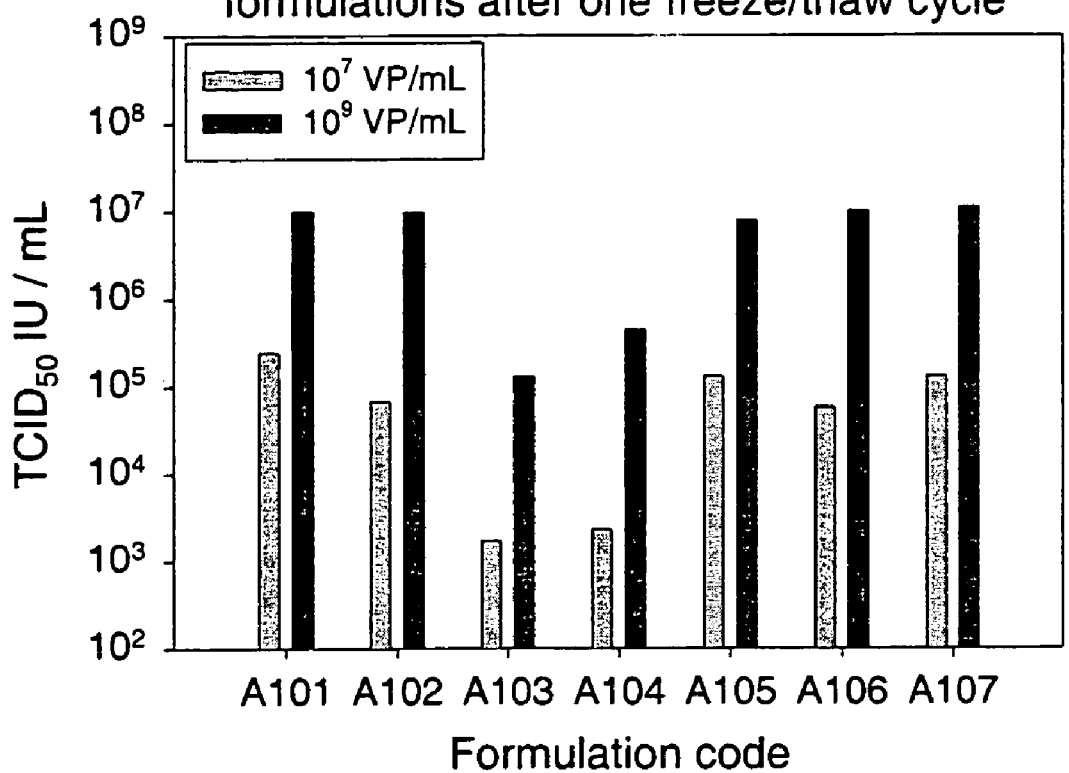
Figure 3. TCID$_{50}$ assay of Ad5gag in candidate formulations after one freeze/thaw cycle

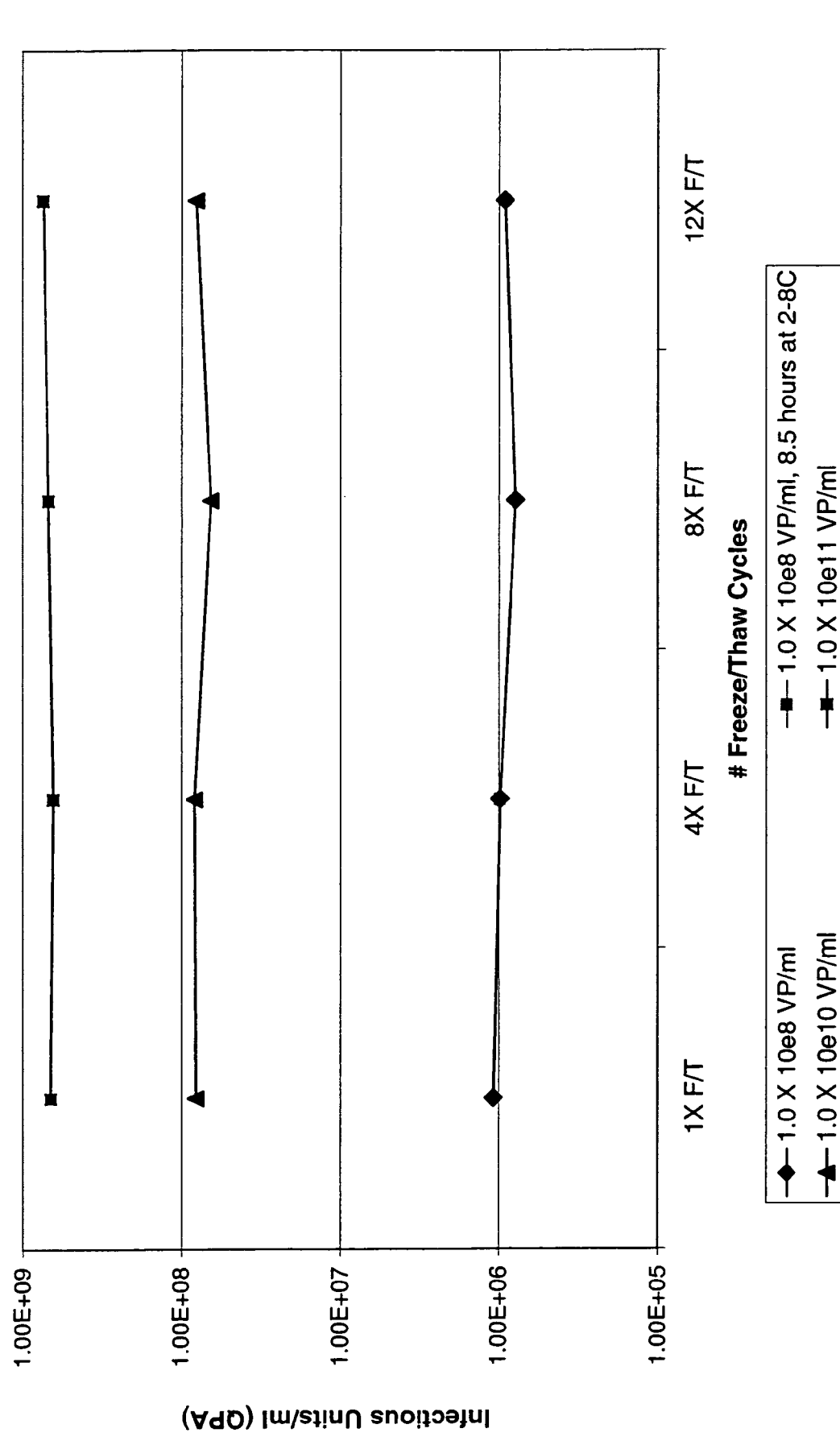

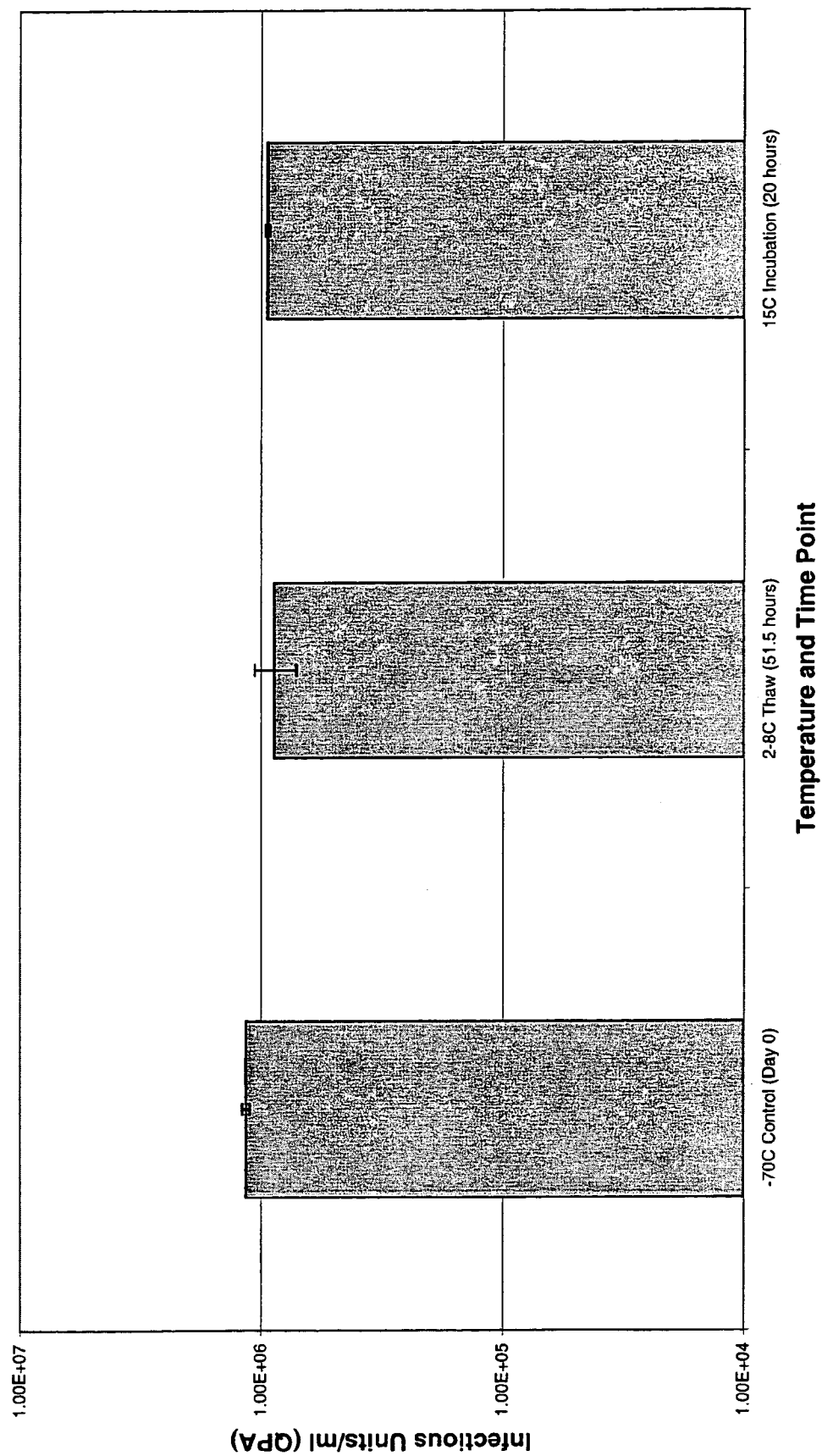
Figure 5. Effect of freeze/thaw on a large aliquot (600 mL) of Ad5FLgag in A105

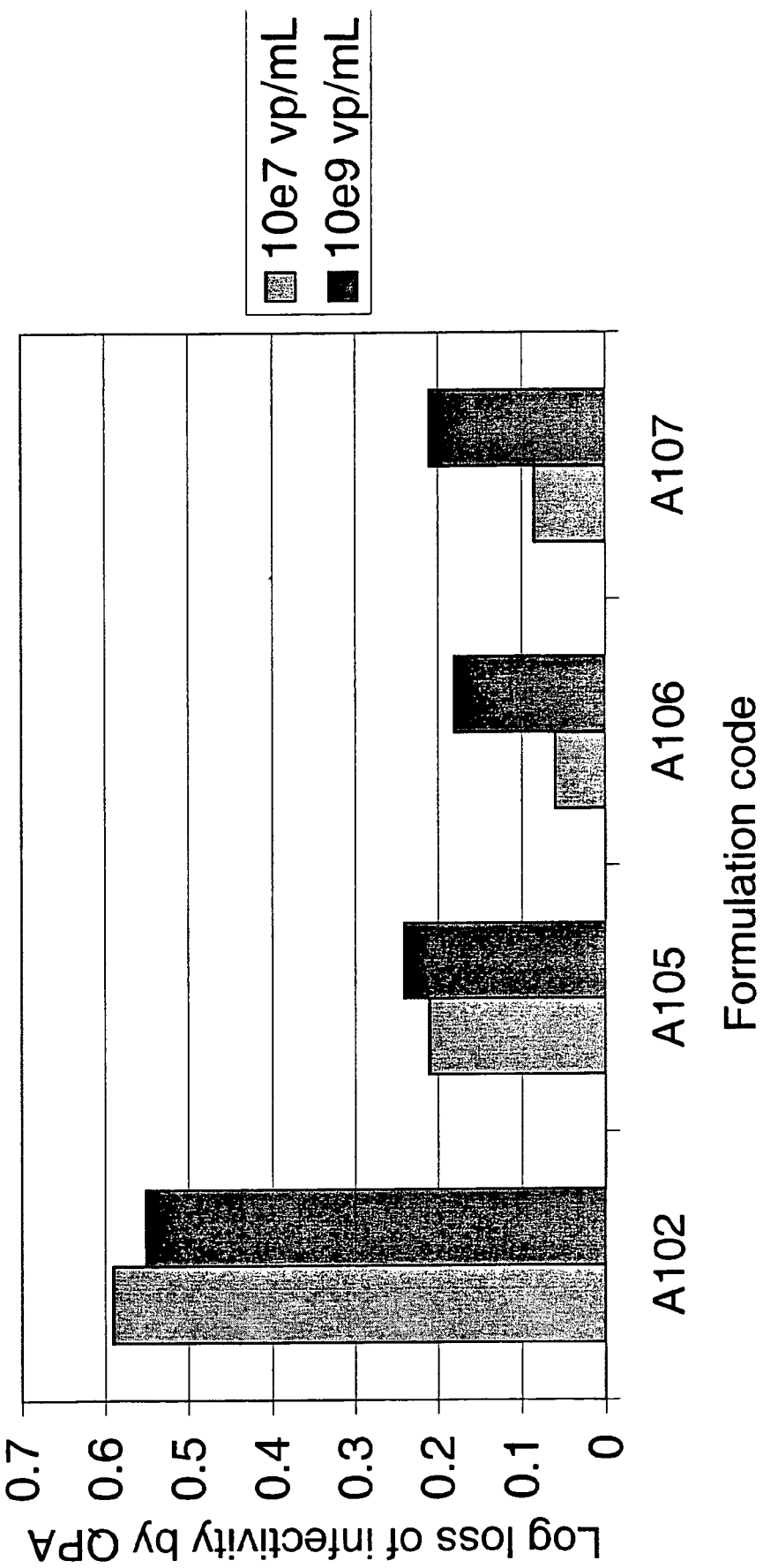

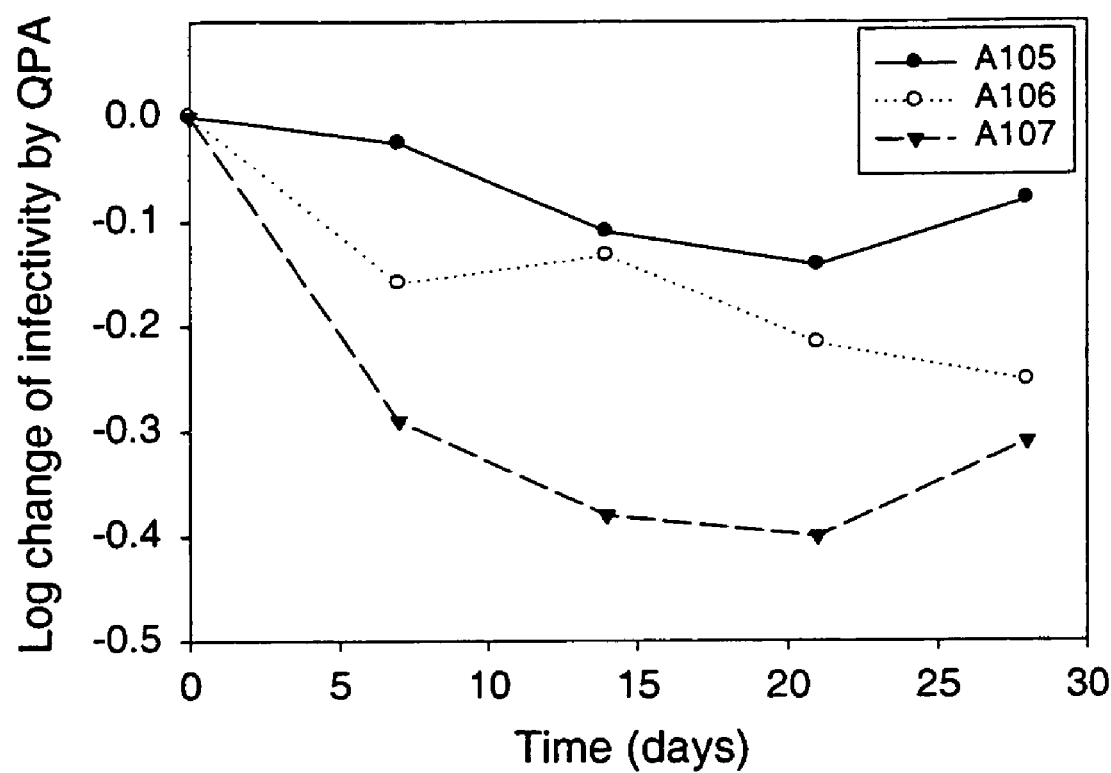
Figure 7. Short-term stability of Ad5gag at 2-8°C

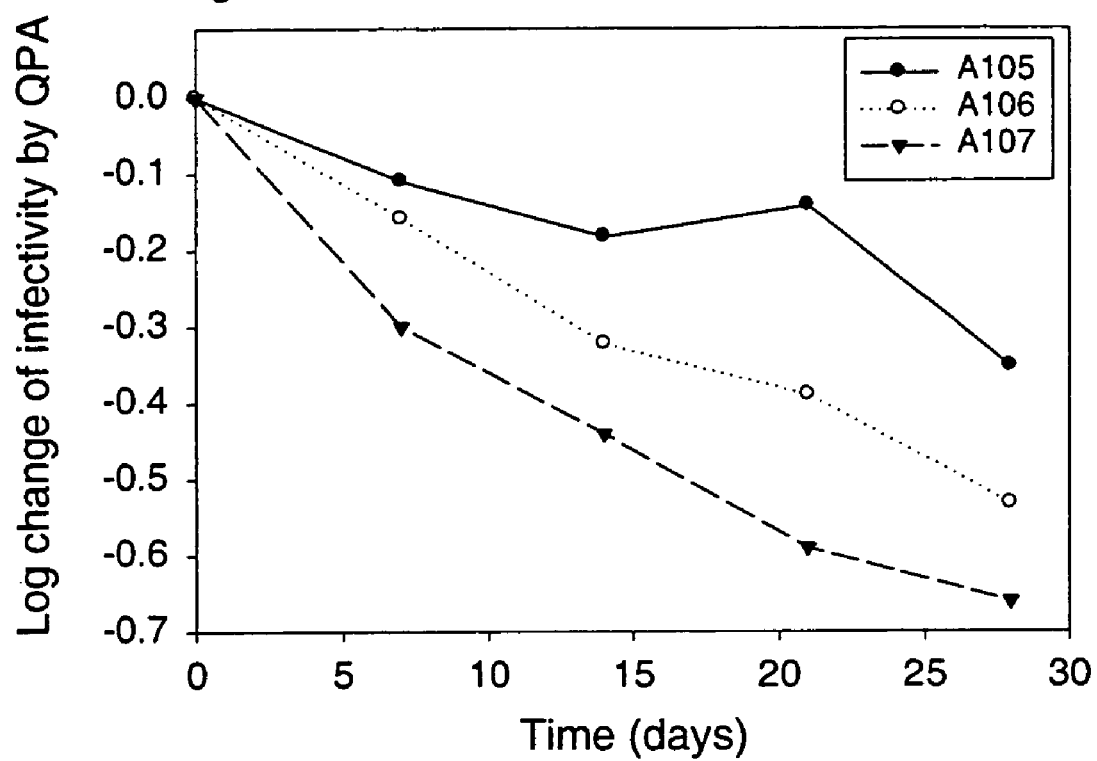

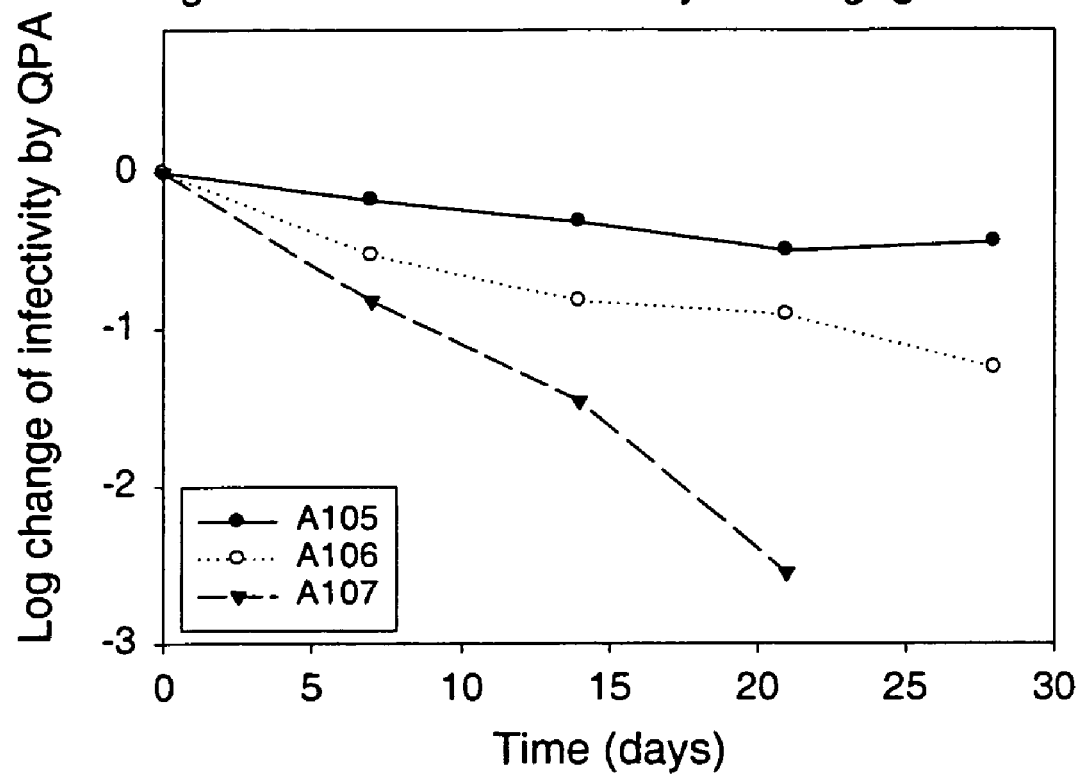

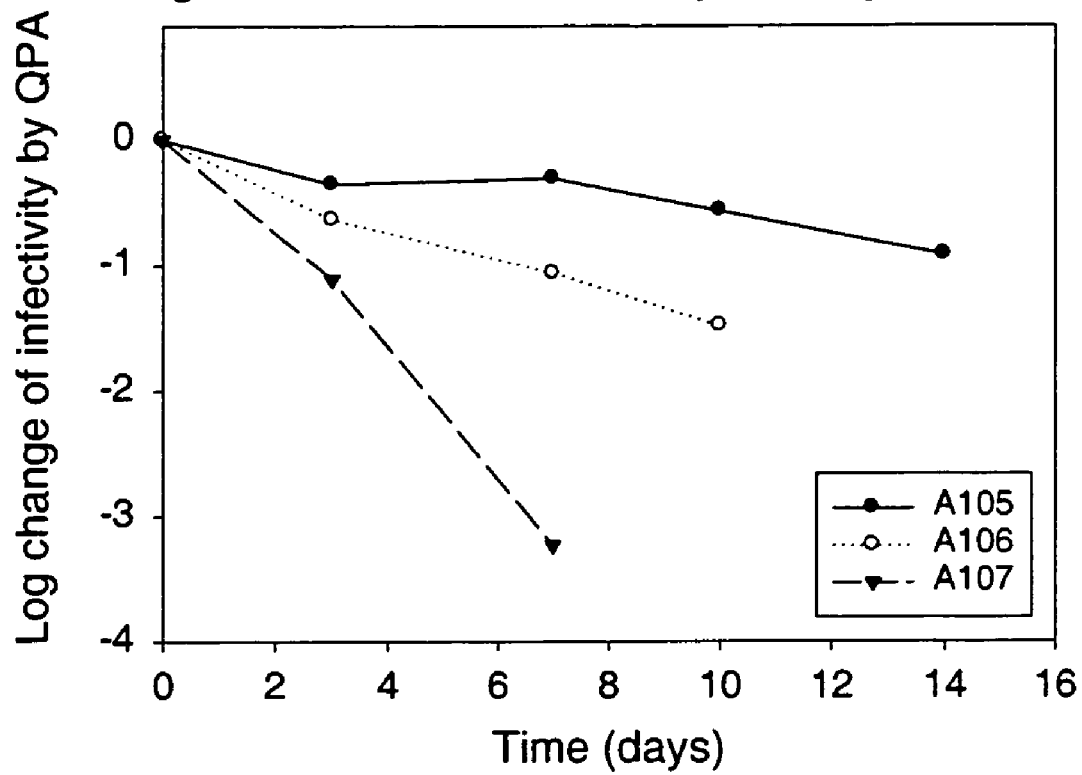
Figure 10. Short-term stability of Ad5gag at 37°C

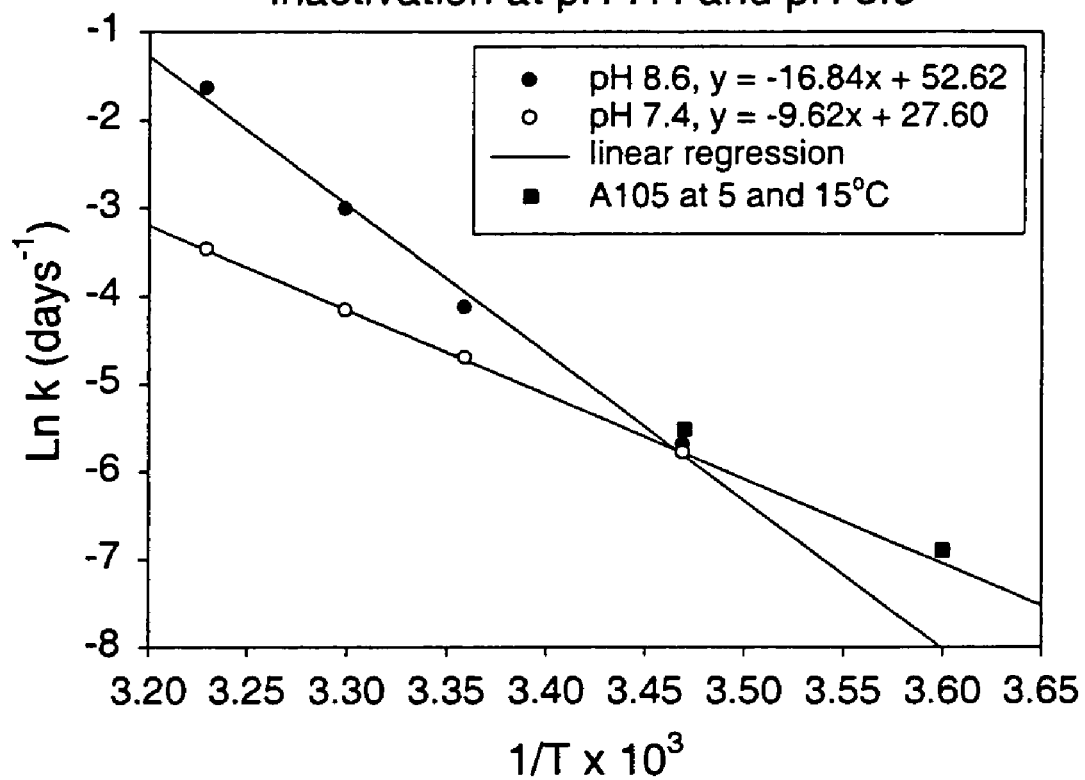
Figure 11. Arrhenius plot of Ad5gag inactivation at pH 7.4 and pH 8.6

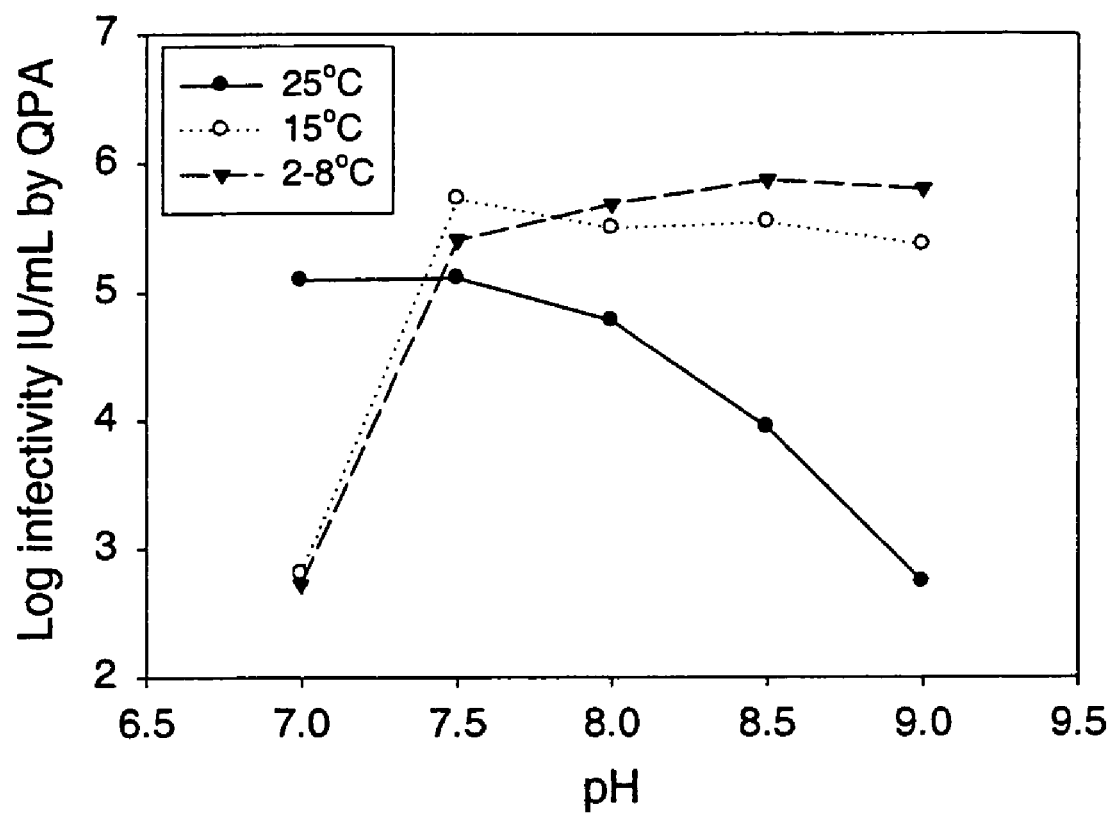
Figure 12. Effect of pH on the stability of Ad5gag

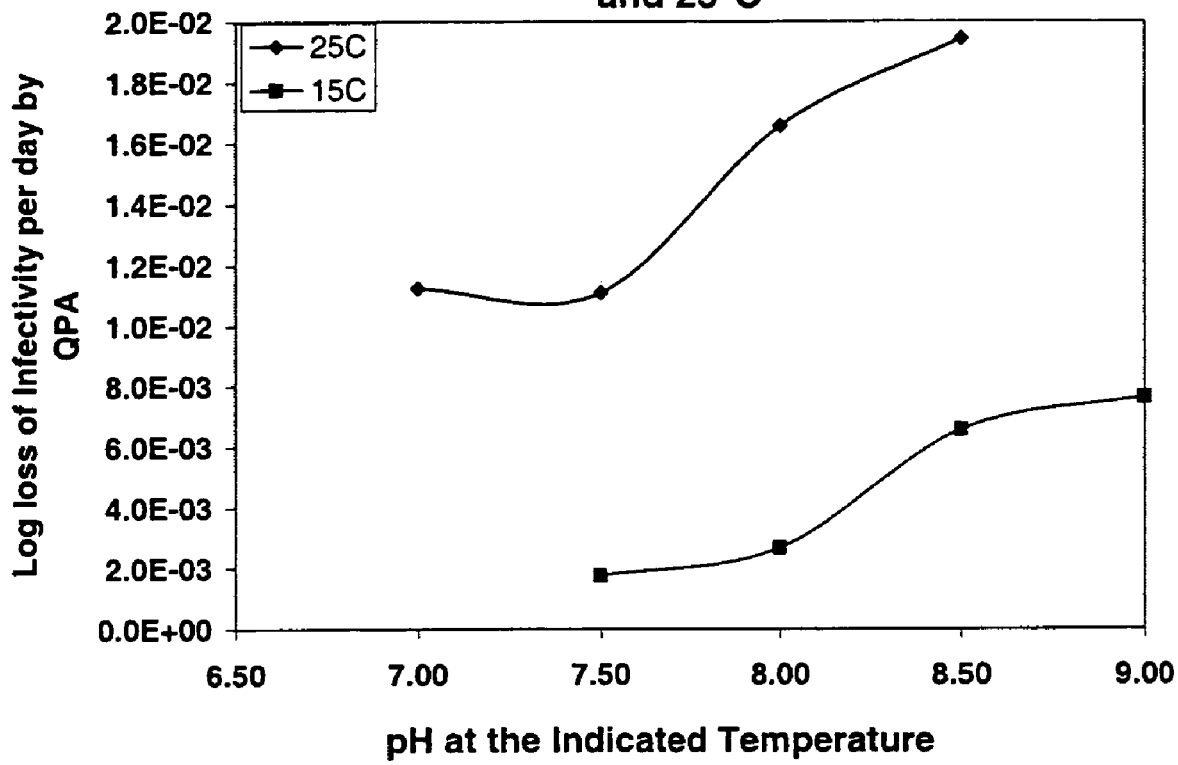
Figure 13. Effect of pH on Ad5gag Stability at 15 and 25°C

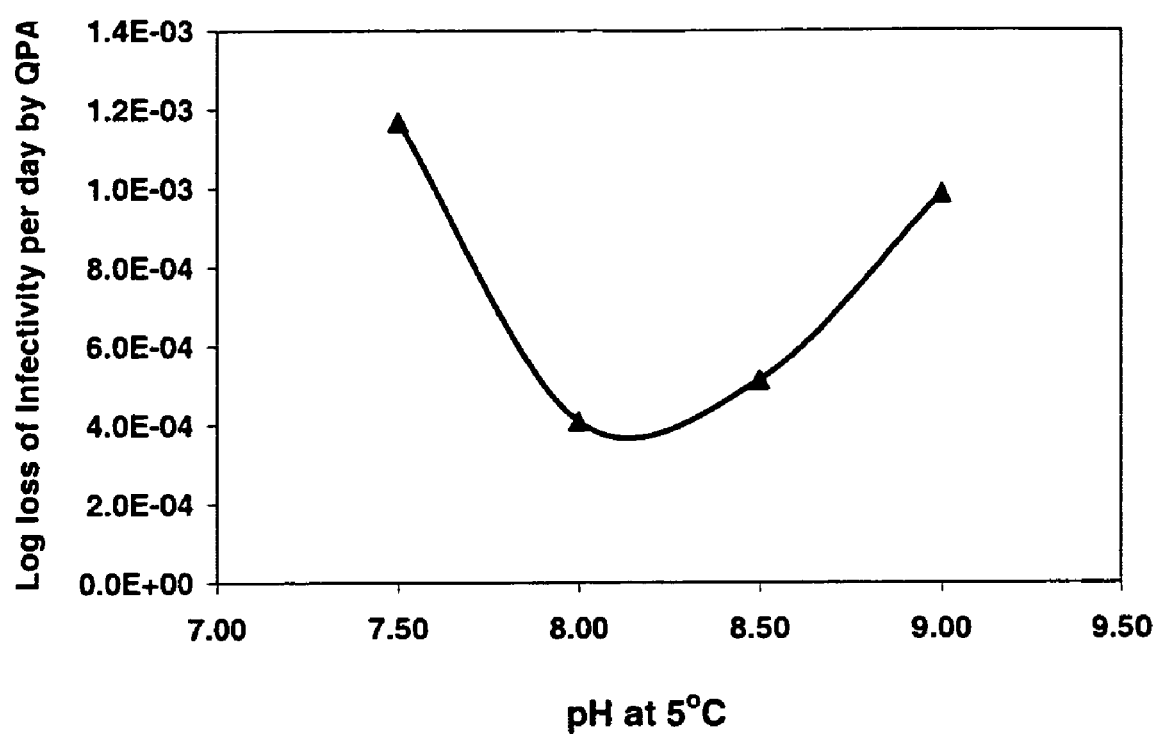
Figure 14. Effect of pH on Ad5gag Stability at 5°C

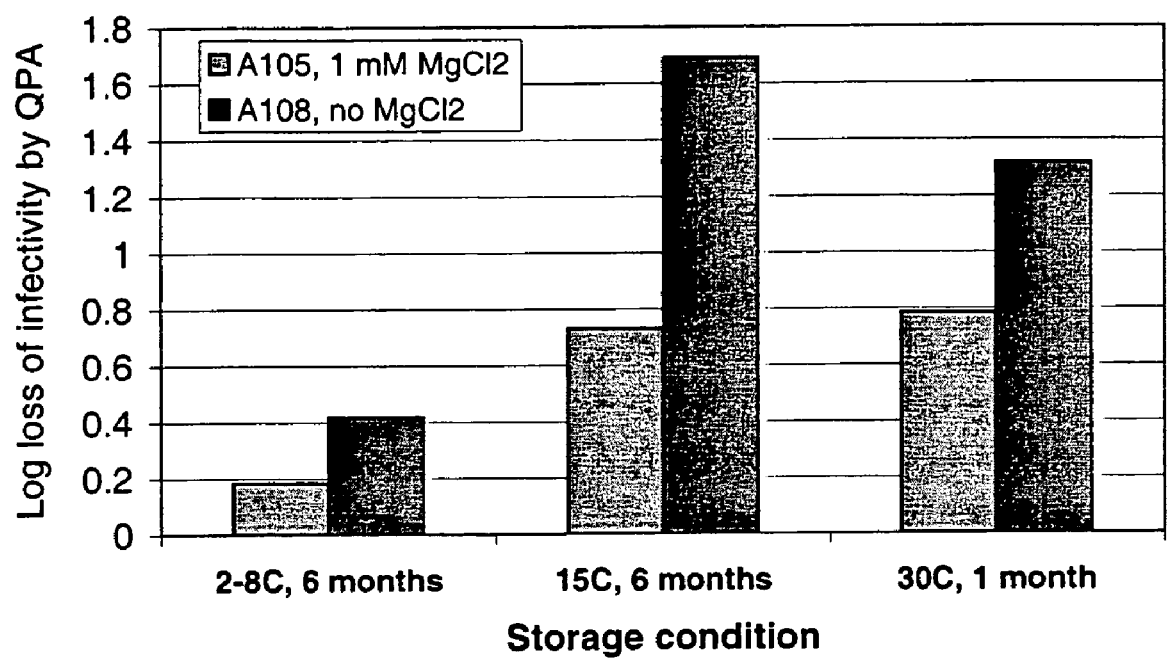
Figure 15. Effect of $MgCl_2$ on the stability of Ad5gag

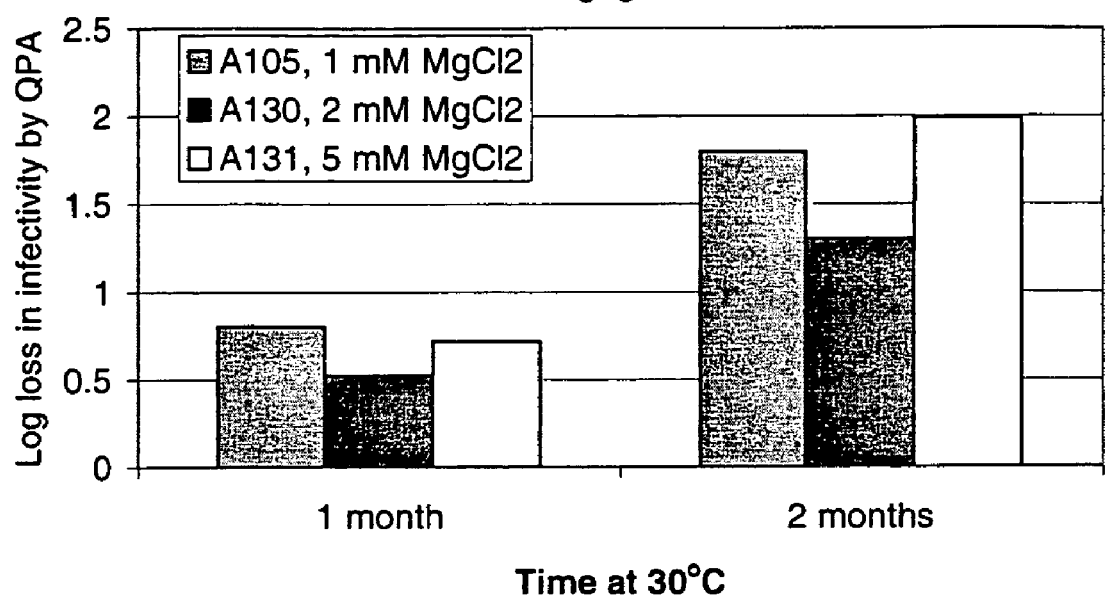
Figure 16. Effect of MgCl$_2$ concentration on the stability of Ad5gag at 30°C

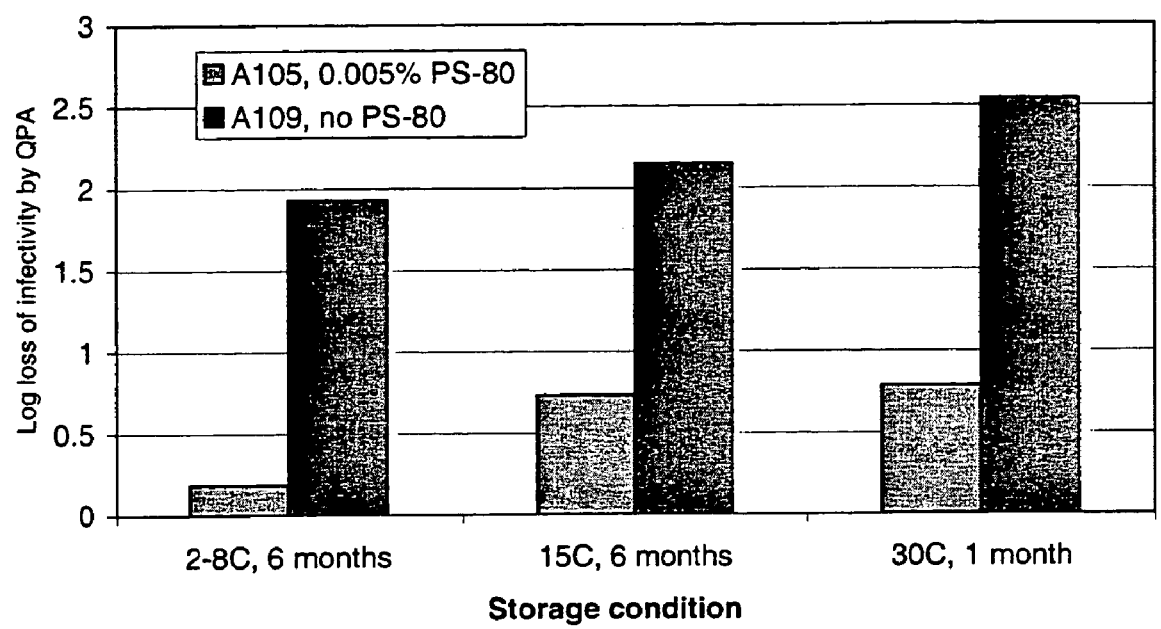
Figure 17. Effect of PS-80 on Ad5gag stability

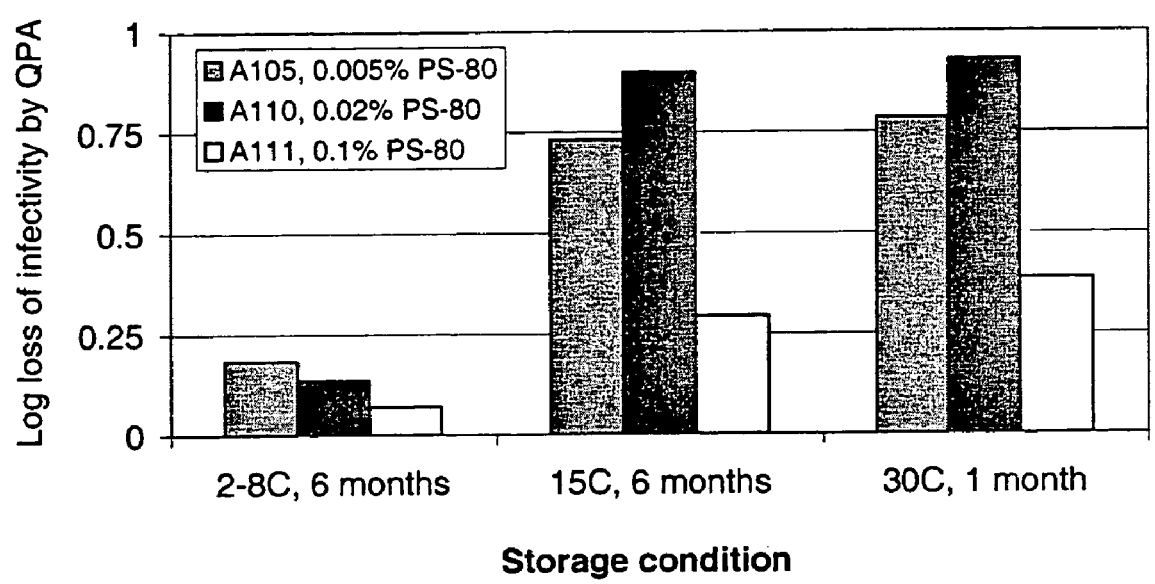
Figure 18. Effect of PS-80 concentration on Ad5gag stability

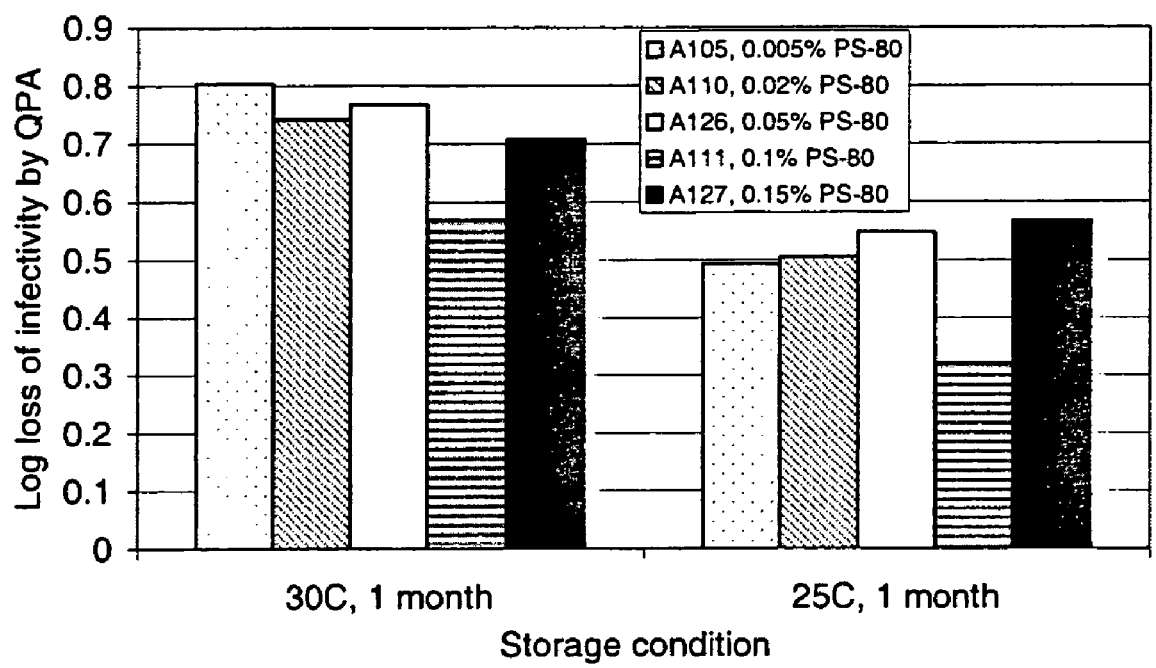
Figure 19. Effect of PS-80 concentration on Ad5gag stability

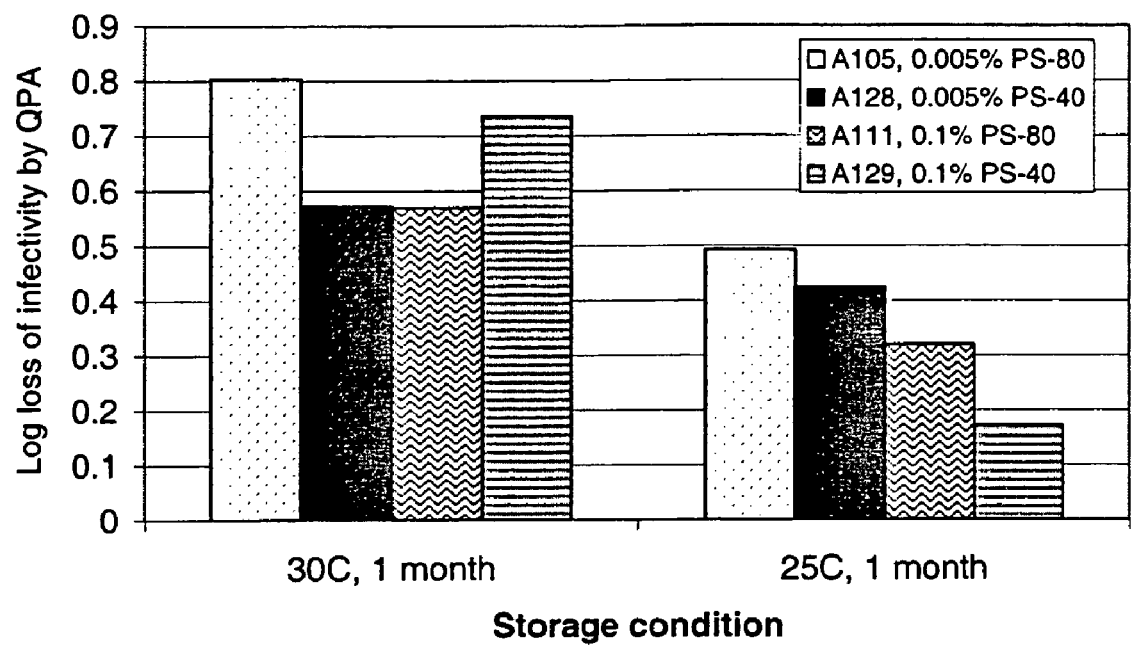
Figure 20. Effect of polysorbate type on the stability of Ad5gag

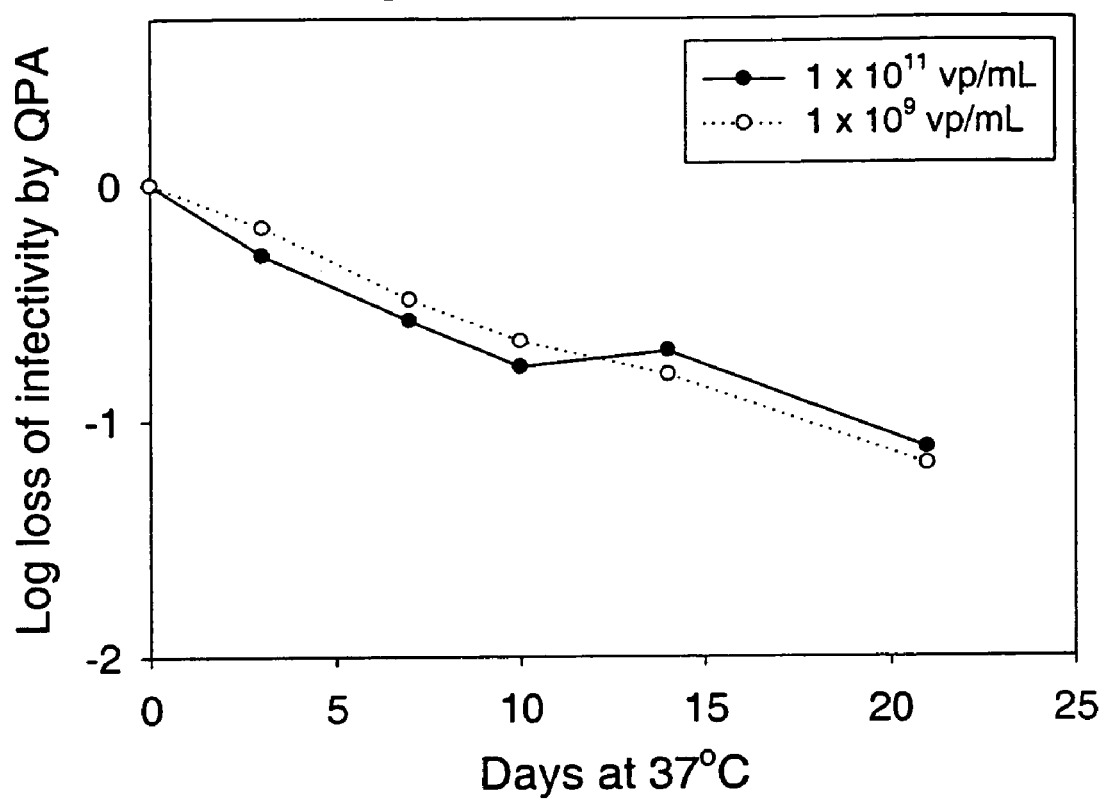
Figure 21. Effect of Ad5FLgag concentration on storage stability at 37°C in A105

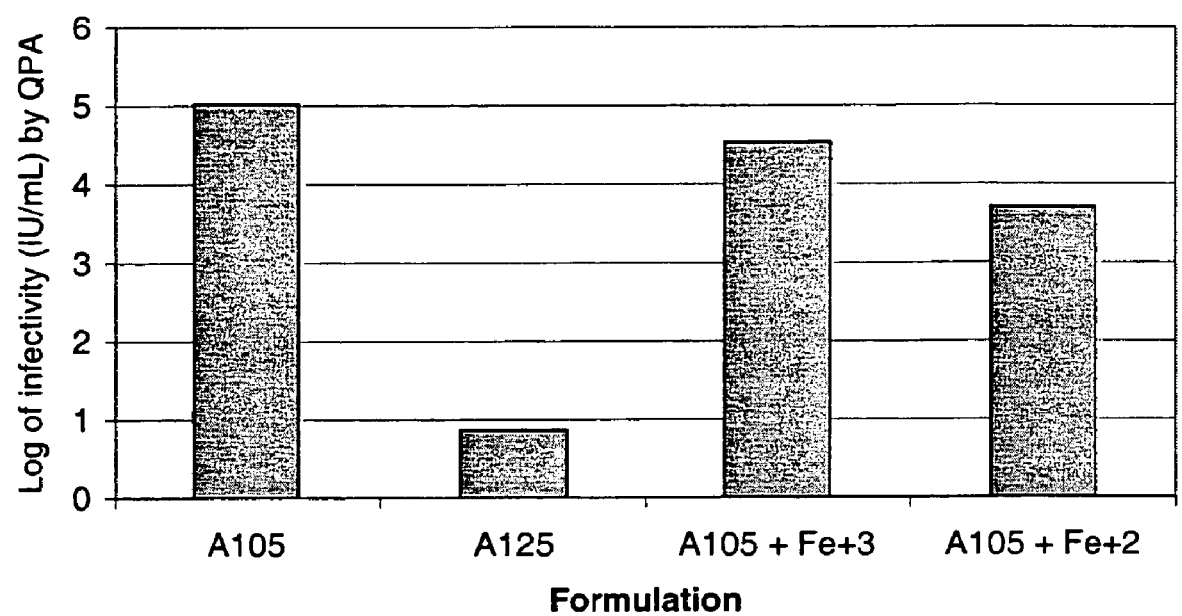
Figure 22. Effect of ascorbic acid and iron on Ad5gag stability

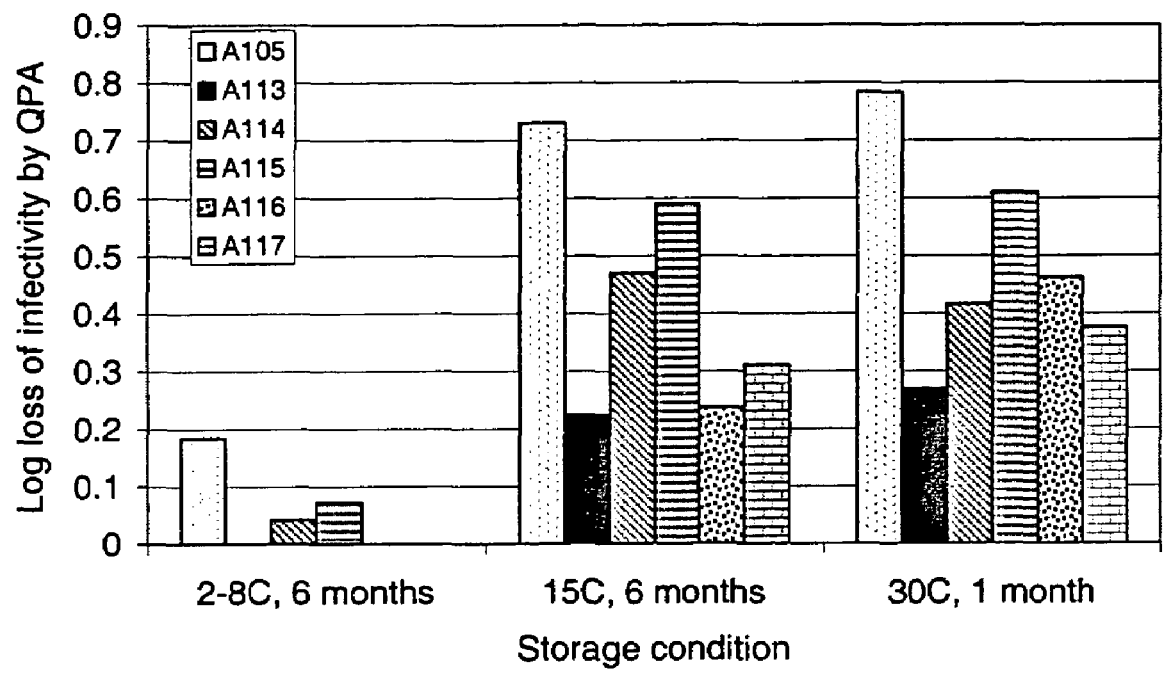
Figure 23. Effect of oxidation inhibitors on Ad5gag stability

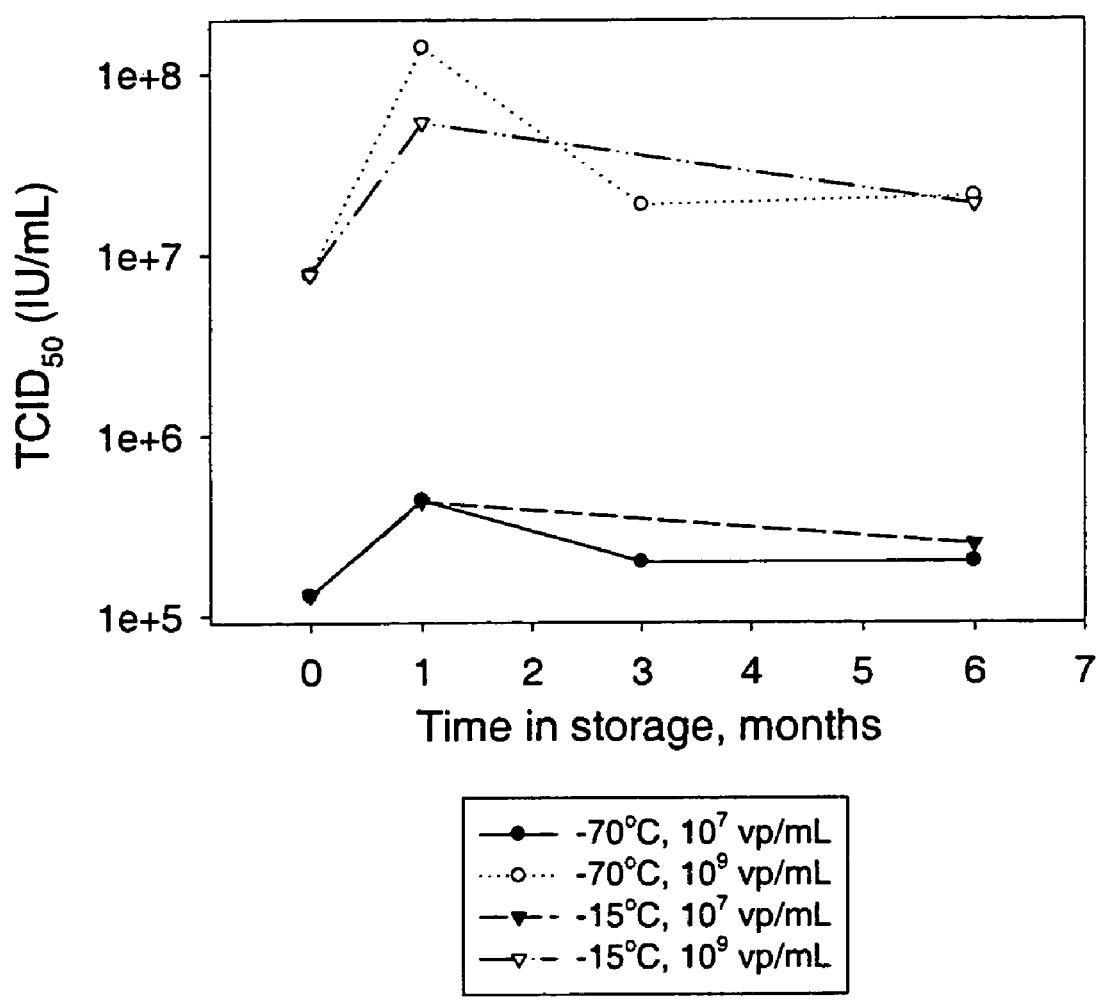

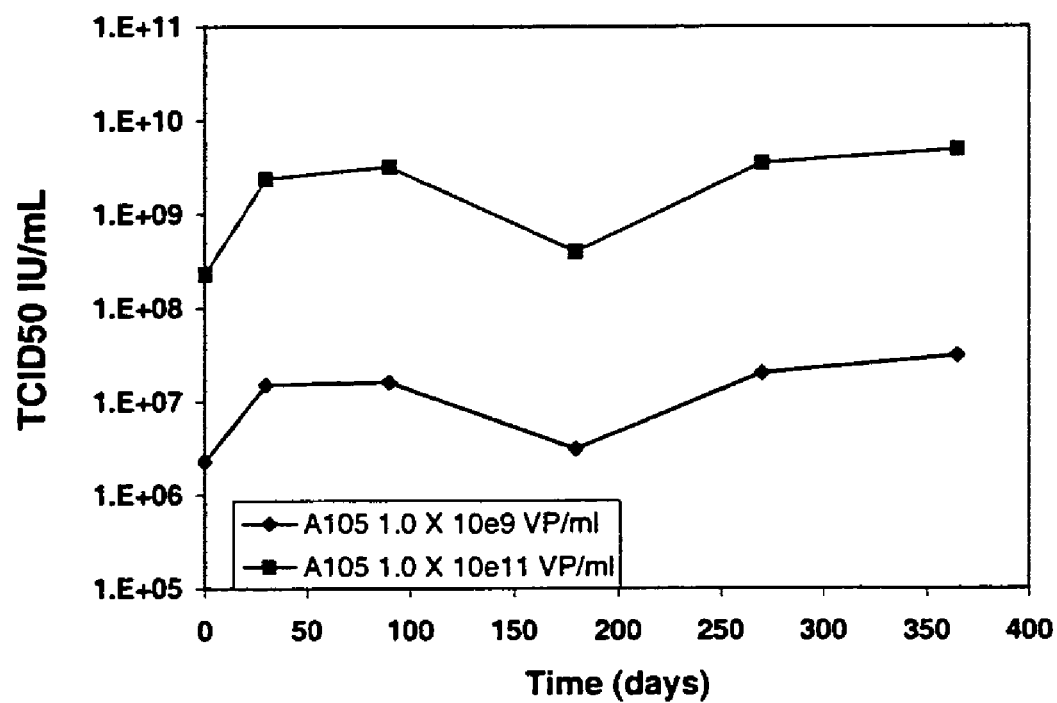
Figure 25. Stability of Ad5gag in A105 at -70C

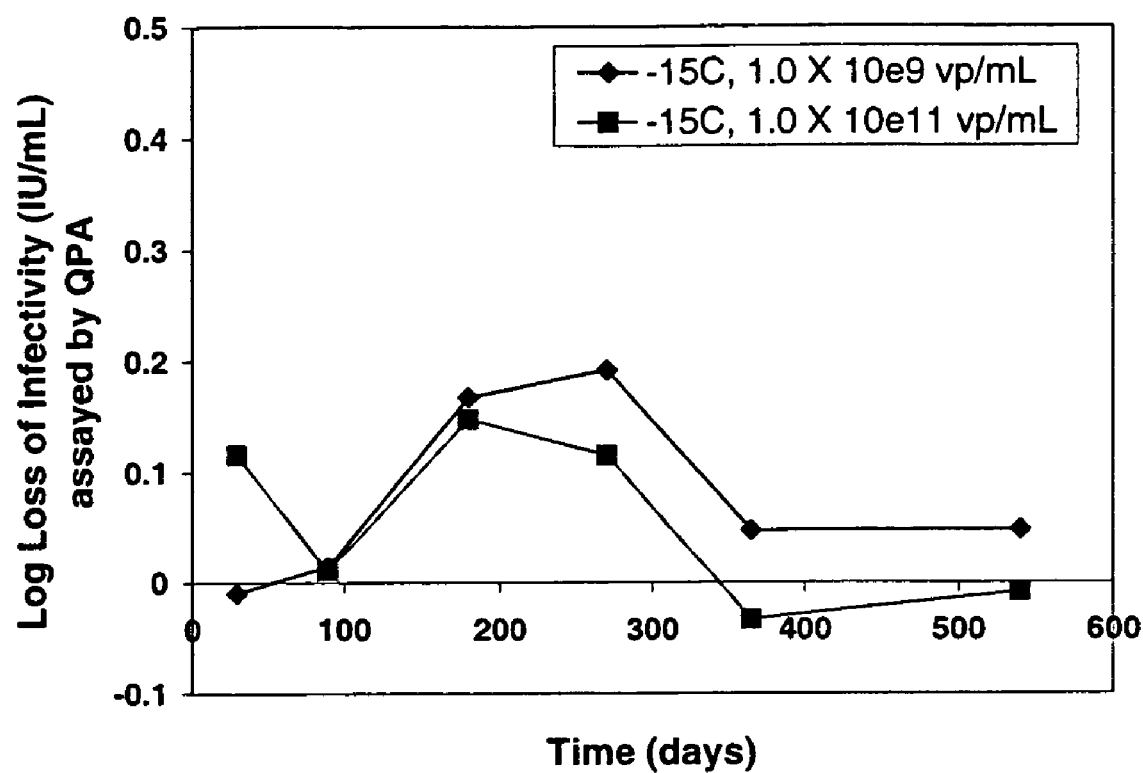
Figure 26. Stability of Ad5gag in A105 at -15°C

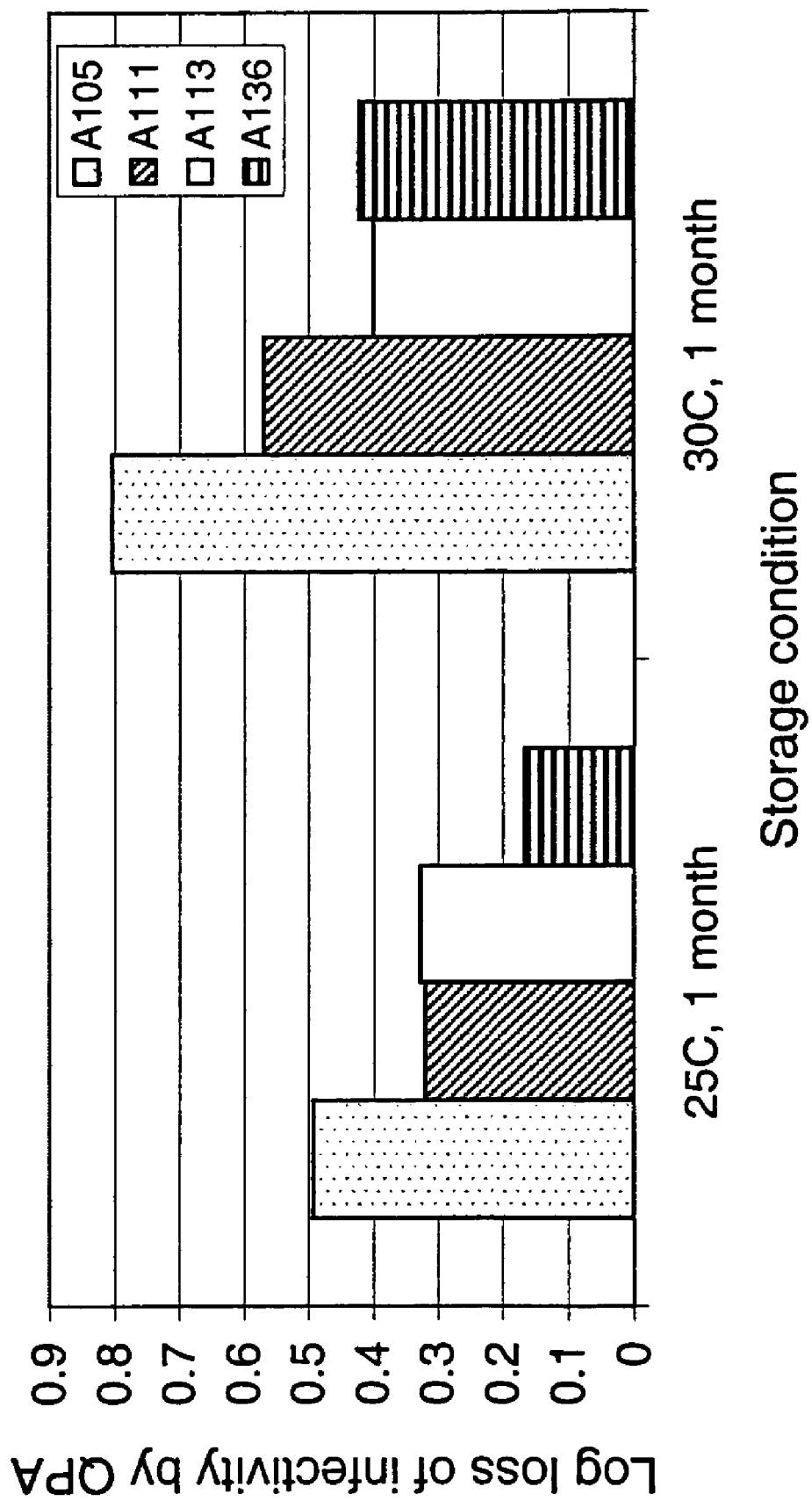
Figure 27. Effect of combining 0.1% PS-80 and EDTA/EtOH on Ad5gag stability

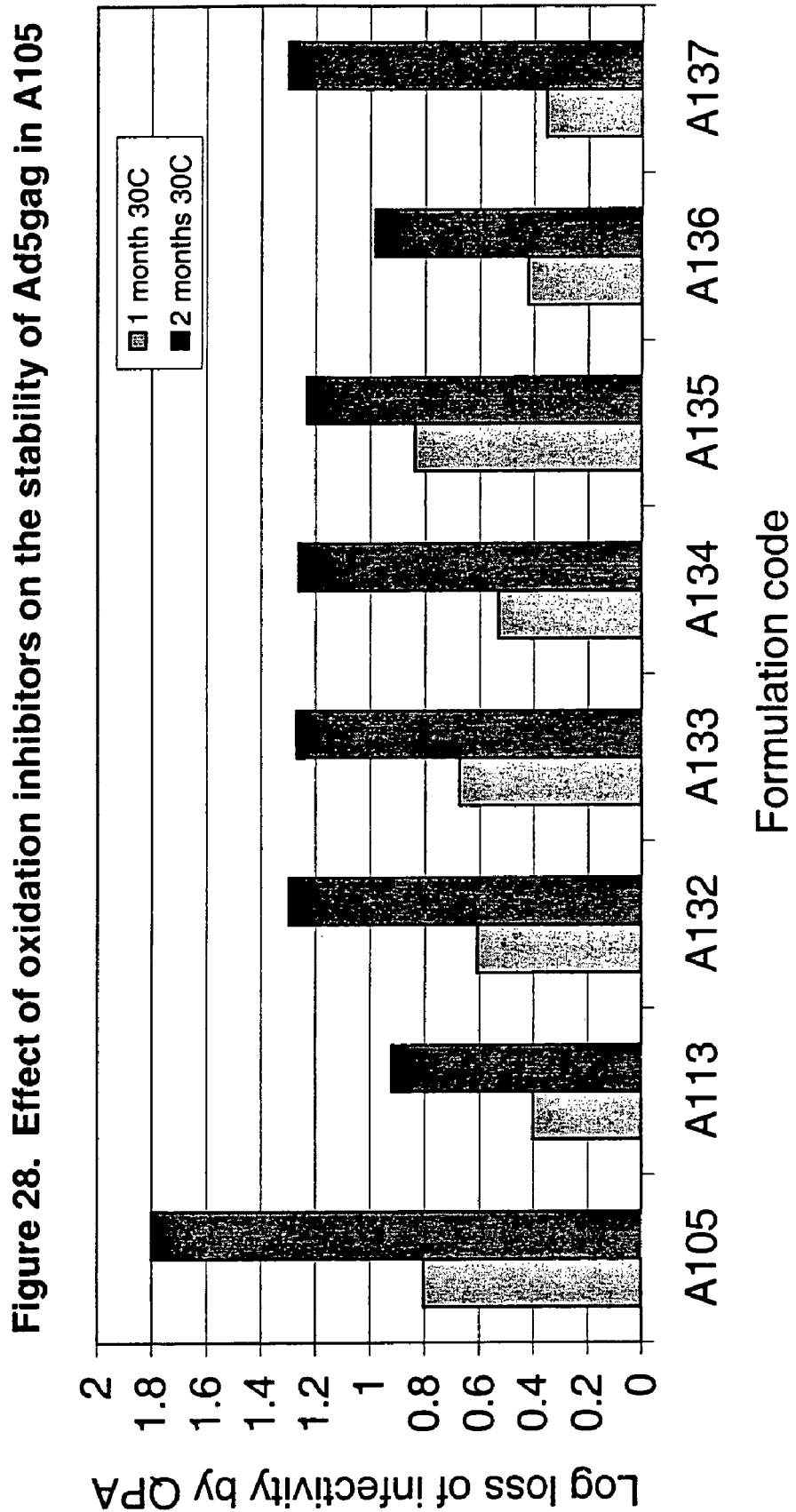

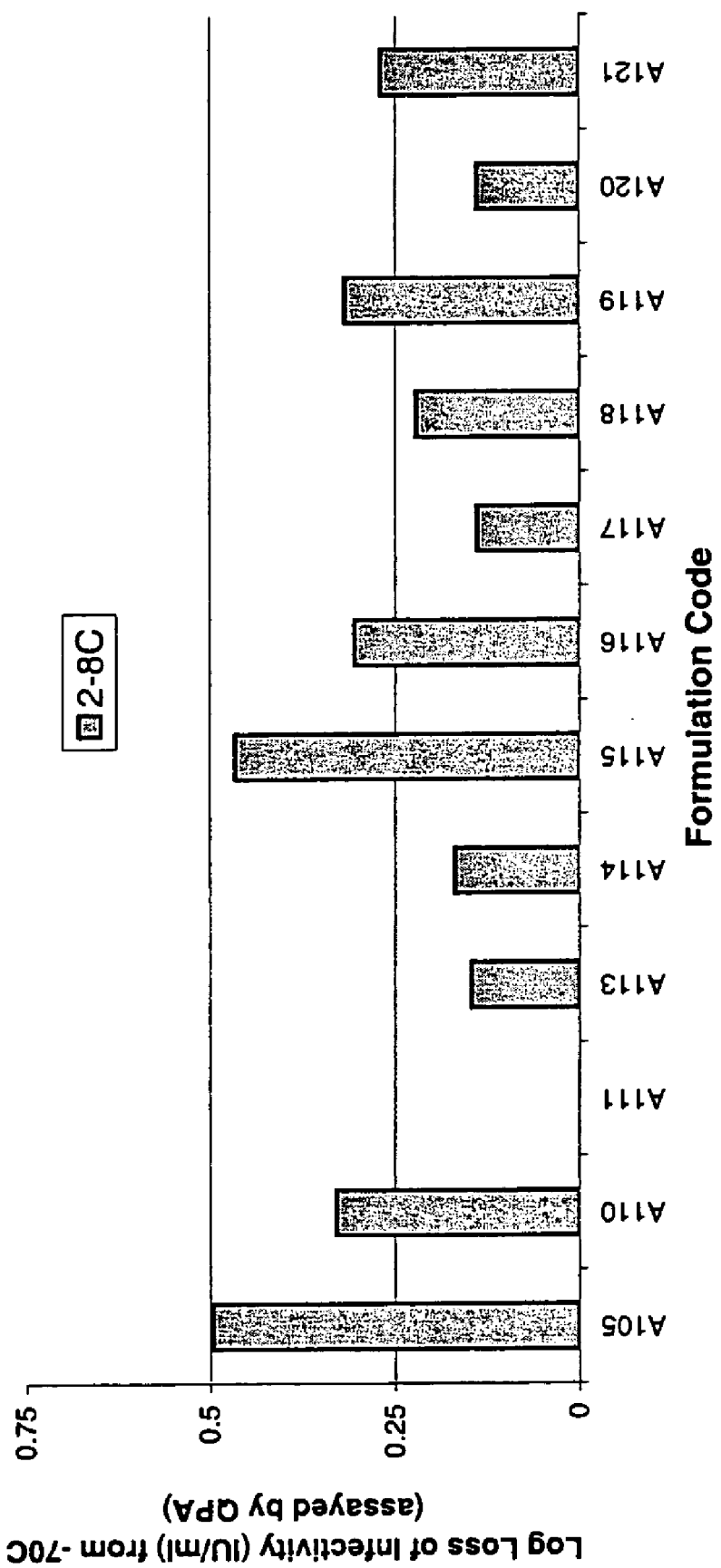

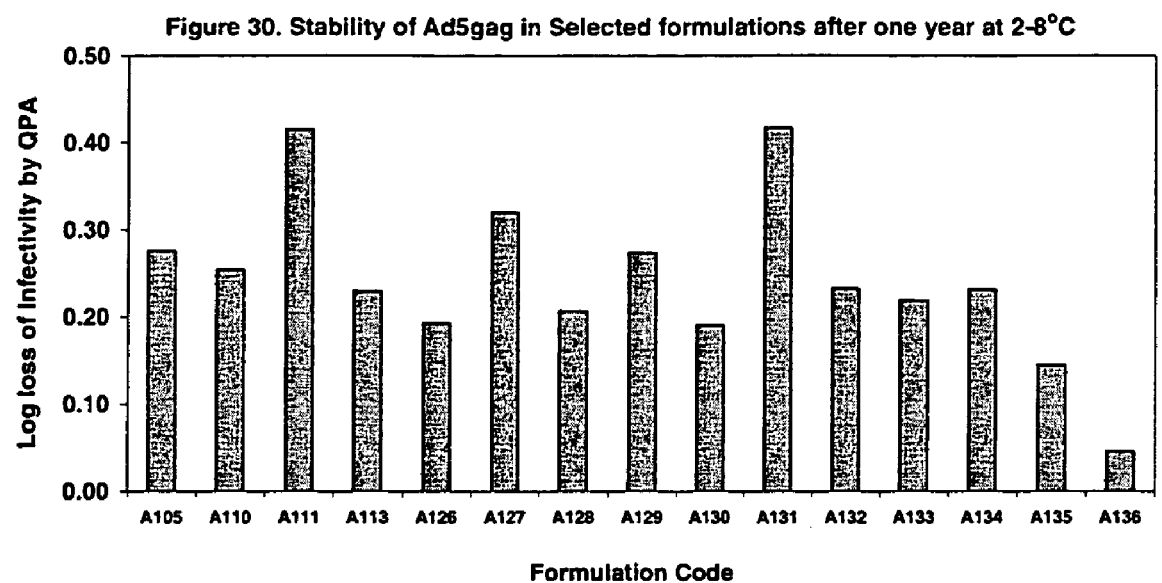
Figure 30. Stability of Ad5gag in Selected formulations after one year at 2-8°C

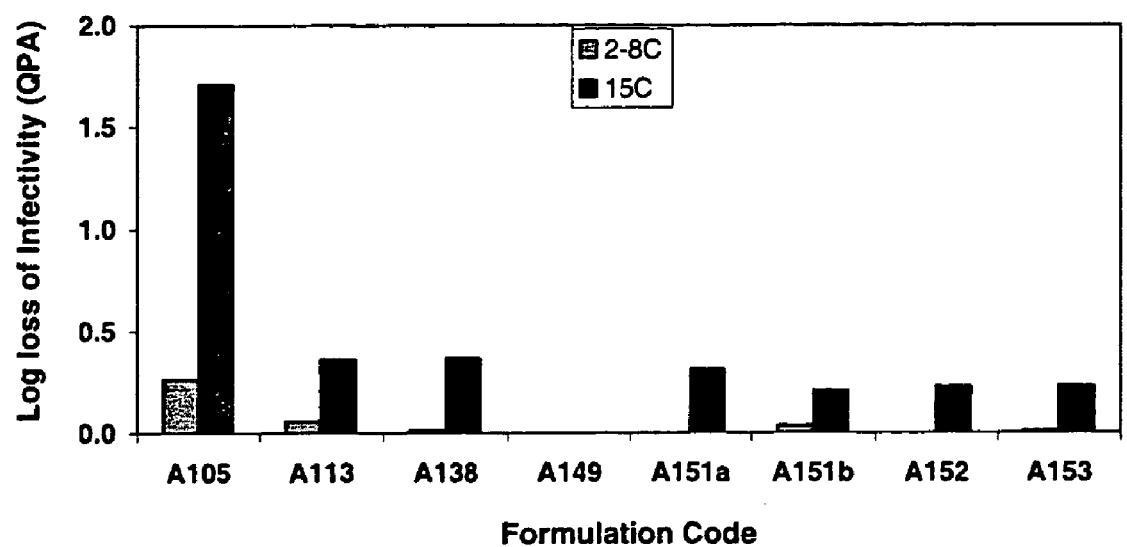
Figure 31. Stability of Ad5gag in Selected Formulations after 9 months of Storage at 2-8°C and 15°C

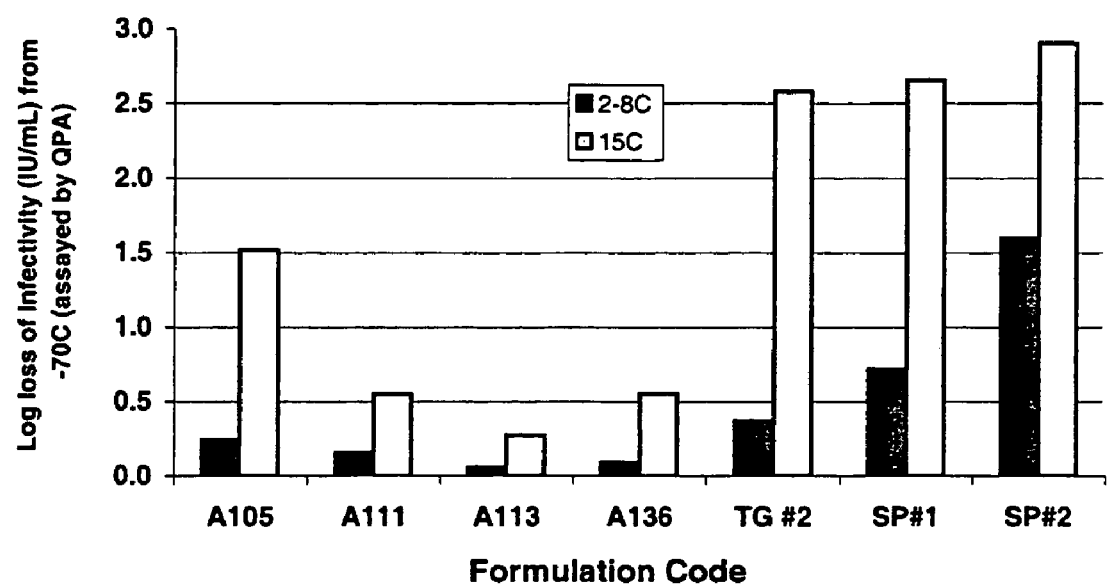
Figure 32. Stability of Ad5gag Candidate Formulations after 9 months of storage at 2-8°C and 15°C

ADENOVIRUS FORMULATIONS

CROSS-REFERENCE TO RELATED APPLICATIONS

This application is a continuation of U.S. application Ser. No. 09/799,937, filed Mar. 6, 2001, abandoned, which claims benefit, under 35 U.S.C. §119(e), to U.S. provisional application Ser. No. 60/187,440, filed Mar. 7, 2000.

STATEMENT REGARDING FEDERALLY-SPONSORED R&D

Not Applicable

REFERENCE TO MICROFICHE APPENDIX

Not Applicable

FIELD OF THE INVENTION

The present invention relates to viral formulations and related pharmaceutical products for use in gene therapy and/or vaccine applications. Especially preferred viral formulations disclosed herein are liquid adenovirus formulations, which show improved stability when stored in about the 2-8° C. range while also being compatible with parenteral administration. These formulations may comprise a buffer, a sugar, a salt, a divalent cation, a non-ionic detergent, as well as a free radical scavenger and/or chelating agent to inhibit free radical oxidation. An especially preferred stabilized virus formulation disclosed herein is a formulation based on inclusion of one or a combination of excipients that inhibit free radical oxidation, which are shown herein to increase stability of adenovirus formulations over commercially acceptable periods of time in about the 2-8° C. range.

BACKGROUND OF THE INVENTION

An ongoing challenge in the field of gene therapy and vaccine research is to generate liquid virus formulations which are stable for longer periods of time within a useful temperature range, such as from about 2° C. to about 8° C. Adenovirus vectors are currently considered one of the leading approaches for gene delivery/therapy. Because of the great potential for adenoviruses in the field of gene therapy, there remains a need for virus formulations that are suitable for human parenteral use, and have a 1-2 year shelf-life at 2-8° C. Although the U.S. military has developed live adenovirus vaccines for human use, they were lyophilized formulations delivered as oral dosage forms in enteric coated capsules (Chanock, et al., 1966, *J. Am. Med. Assoc.* 195: 151-158; Griffin, et al., 1970, *Arch. Intern. Med.* 125: 981-986; Top, et al., 1971, *J. Infect. Dis.* 124: 148-154). The excipients used in these early lyophilized formulations (gelatin, skim milk, human serum albumin) make these lyophilized formulations very unattractive for human parenteral administration. Despite reports on the structure and characterization of adenoviruses, there has been little published on the development of stabilization and formulation of adenovirus for parenteral administration in humans. Furthermore, most of the formulation work concerns lyophilized rather than aqueous formulations, presumably because the prospects for a stable liquid formulation seemed rather poor.

There are some limited reports of liquid formulations of adenovirus with stability data.

WO99/41416 discloses virus formulations which contain glycerol, sodium phosphate, Tris, sucrose, $MgCl_2$, and polysorbate 80. The most stable formulation reported lost 0.52 logs of infectivity in one year at 4 C.

WO98/02522 discloses virus formulations with concentrations of sucrose from about 0.75M to 1.5M sucrose. Such a formulation would not be acceptable for human parenteral use.

Nyberg-Hoffman et al. (1999, *Nature Medicine* 5 (8): 955-956) disclose frozen liquid adenoviral formulations which contain Tris, sucrose and $MgCl_2$.

Croyle et al. (1998, *Pharm. Dev. Technol.* 3 (3): 373-383) disclose lyophilized, frozen liquid and liquid virus formulations that contain Tris and phosphate buffered solutions with high concentrations of sucrose, trehalose or sorbitol/gelatin.

Therefore, the need remains for the development of a recombinant virus liquid formulation that is stable for approximately 1-2 years at 2-8° C. and compatible with parenteral administration. Such a liquid formulation offers advantages such as lower overall cost, decreased development time and ease of use for the customer. The present invention addresses and meets these needs by disclosing improved recombinant virus liquid formulations which show enhanced stability for longer periods of time at temperatures in the range of 2-8° C.

SUMMARY OF THE INVENTION

The present invention relates to stabilized virus formulations and related pharmaceutical products for use in gene therapy and/or vaccine applications. A preferred viral formulation, as disclosed herein, may related to liquid formulations which comprise a recombinant adenovirus, formulations which show improved viral stability when stored in about the 2-8° C. range and higher while also being compatible with parenteral administration. These formulations may comprise a buffer, a sugar, a salt, a divalent cation, a non-ionic detergent, as well as additional components which enhance stability of the included virus, including but not limited to a free radical scavenger and/or a chelating agent. The adenoviral-based formulations of the present invention are amenable to prolonged storage at 2° C. to 8° C. and higher for periods approaching two years. The recombinant viruses of the present invention which show enhanced storage stability include but are not limited to adenovirus, adeno-associated virus, retroviruses, herpes virus, vaccinia virus, rotovirus, pox viruses. The preferred virus is an adenovirus, including but not limited to human Ad5, Ad2, Ad6, Ad24 serotypes, and especially recombinant adenoviral virus for use in human gene therapy or human gene-based vaccination technology, including a prophylactic or therapeutic application utilizing such a gene-based vaccination technology.

The formulations of the present invention are (i) optimally a buffered solution and further comprise (ii) a minimal amount of at least one non-ionic surfactant; (iii) a divalent cation; (iv) a cryoprotectant; (v) a salt, and (vi), preferably inclusion of one or more additional excipients that act as inhibitors of free radical oxidation. The formulations of the present invention rely on a useful range of total osmolarity which promotes long term stability at temperatures of 2-8° C., or higher, while also making the formulation useful for parenteral, and especially intramuscular, injection.

To this end, a first embodiment of the present invention relates to a series of adenovirus formulations (including but not limited to a recombinant adenovirus) which comprise Tris as the buffer, sucrose as the cryoprotectant, NaCl as the salt, $MgCl_2$ as the divalent cation and either Polysorbate-80 or Polysorbate-40 as the surfactant.

A second embodiment of the present invention relates to inclusion of one or more inhibitors of free radical oxidation, including both metal ion chelators and hydroxyl radical scavengers, which are shown herein to enhance short and long term stability of the virus formulations described herein (again, including but not limited to an adenovirus, including a recombinant adenovirus containing a transgene, or portion thereof, which is useful in gene therapy and/or gene vaccination technology). Therefore, a preferred embodiment of the present invention is a viral formulation which contains one or more components which act as an inhibitor of free radical oxidation. It is shown herein that addition of these components enhance long term stability at temperatures up through the 2-8° C. range, or higher, when compared to core formulations which do not contains these inhibitors. These formulations are also compatible with parenteral administration. To this end, the present invention relates to a virus formulation which contains at least one inhibitor of free radical oxidation which effectively enhances stability of the virus-containing formulation. While the exemplified adenovirus-based formulations such as A113 represent a preferred formulation, these formulations in no way suggest a limitation to additional formulations and methods of use based on alternative formulations components.

A third core embodiment of the present invention comprises inclusion, alone or in combination with free radical oxidation inhibitors, an effective amount of plasmid DNA, which is shown to effectively increase the long term stability of a virus formulation and conditions as described throughout this specification. Therefore, the present invention also relates to a virus formulation which contains an amount of a nucleic acid such that addition of the nucleic acid effectively enhances stability of the virus-containing formulation.

The enhanced long-term stability up through the 2-8° C. range results in an extended shelf life of the virus formulations disclosed herein, allowing for storage and eventual host administration of these liquid formulations over about a 1-2 year period with acceptable losses in virus infectivity. In addition, formulations of the present invention show stability through extended freeze/thaw cycles.

BRIEF DESCRIPTION OF THE DRAWINGS

FIG. 1 shows the effects of one freeze/thaw cycle (from −70° C. to 5° C.) on the recovery/stability of Ad5gag in formulations A101 through A107.

FIG. 2 shows the effect of 1 to 3 freeze/thaw cycles on the recovery/stability of Ad5gag in formulations A101 through A107.

FIG. 3 shows the loss of infectivity of Ad5gag in formulations A101 through A107.

FIG. 4 shows the effect of 12 freeze/thaw cycles on the stability of Ad5gag in A105 at $10^8$, $10^{10}$ and $10^{11}$ vp/mL.

FIG. 5 shows the effect that freezing, thawing and a 15° C. incubation have on the infectivity of Ad5gag in A105.

FIG. 6 shows short-term stability (72 hours) of Ad5gag in formulations A102, A105, A106 and A107 at $1\times10^7$ vp/mL and $1\times10^9$ vp/mL.

FIG. 7 shows short-term stability (up to 28 days) of Ad5gag in formulations A105, A106 and A107 at 2-8° C.

FIG. 8 shows short-term stability (up to 28 days) of Ad5gag in formulations A105, A106 and A107 at 15° C.

FIG. 9 shows short-term stability (up to 28 days) of Ad5gag in formulations A105, A106 and A107 at 25° C.

FIG. 10 shows short-term stability (up to 28 days) of Ad5gag in formulations A105, A106 and A107 at 37° C.

FIG. 11 shows an Arrhenius plot of Ad5gag inactivation at pH 7.4 and pH 8.6.

FIG. 12 shows the effect of pH on Ad5gag infectivity at 2-8° C., 15° C. and 25° C.

FIG. 13 shows the effect of pH on the long-term stability (up to 12 months) of Ad5gag at 15° C. and 25° C.

FIG. 14 shows the effect of pH on the long-term stability (12 months) of Ad5gag at 2-8° C.

FIG. 15 shows the effect of $MgCl_2$ on Ad5gag stability at 2-8° C., 15° C. and 30° C.

FIG. 16 shows the effect of $MgCl_2$ concentration on Ad5gag stability at 30° C.

FIG. 17 shows the effect of polysorbate-80 (PS-80) on the stability of Ad5gag at 2-8° C., 15° C. and 30° C.

FIG. 18 shows the effect of polysorbate-80 (PS-80) concentration on the stability of Ad5gag at 2-8° C., 15° C. and 30° C.

FIG. 19 shows the effect of polysorbate-80 (PS-80) concentration on the stability of Ad5gag at 25° C. and 30° C. for one month.

FIG. 20 shows the effect of polysorbate type (PS-80 and PS-40) on the stability of Ad5gag at 25° C. and 30° C.

FIG. 21 shows the effect of virus concentration on stability at 37° C.

FIG. 22 shows the effect of ascorbic acid and iron on Ad5gag stability.

FIG. 23 shows the effect of oxidation inhibitors on Ad5gag stability at 2-8° C., 15° C. and 30° C.

FIG. 24 shows the stability of Ad5gag at −70° C. and −15° C., between $10^7$ and $10^9$ vp/mL.

FIG. 25 shows the stability of Ad5gag in A105 at −70° C. at $10^9$ vp/mL and $10^{11}$ vp/mL.

FIG. 26 shows the stability of Ad5gag in A105 at −15° C. at $10^9$ vp/mL and $10^{11}$ vp/mL.

FIG. 27 shows the effect of combining PS-80 and EDTA/Ethanol on Ad5gag stability at 25° C. and 30° C. for 1 month.

FIG. 28 shows the effect of various oxidations inhibitors on Ad5gag stability at 1 and 2 months at 30° C. as shown with formulations A113, A132, A133, A134, A135, A136 and A137.

FIG. 29 shows the long-term stability of Ad5gag in selected formulations after 18 months of storage at 2-8° C.

FIG. 30 shows the long-term stability of Ad5gag in additional selected formulations after one year of storage at 2-8° C.

FIG. 31 shows the stability of Ad5gag in selected formulations after 9 months of storage at 2-8° C. and 15° C.

FIG. 32 shows the stability of Ad5gag in selected formulations of the present invention compared to Ad5gag stability in formulations disclosed by Transgene and Schering-Plough, after 9 months of storage at 2-8° C. and 15° C.

DETAILED DESCRIPTION OF THE INVENTION

The present invention relates to formulations which stabilize a respective virus component and to related pharmaceutical products, preferably for use in gene therapy and/or vaccine applications. A preferred stabilized virus containing formulation disclosed herein is liquid adenovirus formulation, which shows improved stability when stored in about the 2-8° C. range and higher while also being compatible with parenteral administration. These preferred formulations which are able to stabilize a respective virus (such as a recombinant adenovirus) may comprise a buffer, a sugar, a salt, a divalent cation, a non-ionic detergent, as well as additional components which enhance stability to the added virus, including but not limited to a free radical scavenger and/or a chelating agent (i.e., an inhibitor of free radical oxidation). In addition to excellent viral stability for prolonged periods of time at −70° C. and −20° C., the formulations which comprise various concetrations of adenovirus are amenable to prolonged storage at 2° C. to 8° C. and higher for periods up to at least one to two years. The virus forumulations which may show enhanced long term storage stability include but are not necessarily limited to adenovirus, adeno-associated virus, retroviruses, herpes virus, vaccinia virus, rotovirus, pox viruses. The preferred virus is a human adenovirus, especially a serotype from a subgroup which shows negligible or no tumor growth in animals, such as subgroup C (Ad1, Ad2, Ad5 and Ad6), subgroup D (Ad8, Ad9, Ad10, Ad13, Ad15, Ad17, Ad19, Ad20, Ad22, Ad23, Ad24, Ad25Ad26, Ad27, Ad28, Ad29, Ad30, Ad32, Ad33, Ad36, Ad37, Ad38, Ad39, Ad42, Ad43, Ad44, Ad45, Ad46, and Ad4) and subgroup E (Ad4). For an exhaustive adenovirus classification scheme, see *Fundamental Virology*, $3^{rd}$ Edition, Ch. 30 @ page 980, Ed. Fields, et al. 1996, Lippincott-Raven. Especially preferred serotypes are selected C serotypes Ad5, Ad2, and Ad6 and subgroup D serotype Ad24. With the guidance provided by this specification, the skilled artisan may adapt the formulations dislcosed herein to non-exemplified adenovirus serotyoes as well as other viruses. To this end, the present invention relates to the use of these formulations to stabilize alternative purified virus, and to the compositions thereof.

The formulations of the present invention provide stability to adenovirus at varying degrees of virus concentration and may be administered to a variety of vertebrate organisms, perferably mammals and especially humans. The stabilized viral formulations of the present invention are preferably recombinant adenovirus-based compositions, wherein administed as a vaccine, for example, may offer a prophylactic advantage to previously uninfected individuals and/or provide a therapeutic effect by reducing viral load levels within an infected individual, thus prolonging the asymptomatic phase of a particular microbial infection, such as an HIV infection. A preferred aspect of the invention is a recombinant adenovirus formulation (i.e., an adenovirus containing a whole or a portion of a transgene which is expressed within the target host subsequent to host administration, such as in any mammalian/human gene therapy- or gene vaccination-based methodology available to the skilled artisan) which shows enhanced stability characteristics described herein with a virus concentration in the range from about $1\times10^7$ vp/mL (virus particles/millileter) to about $1\times10^{13}$ vp/mL. A more preferred range is from about $1\times10^9$ to $1\times10^{12}$ vp/mL, with an especially preferred virus concentration being from about $1\times10^{11}$ to $1\times10^{12}$ vp/mL. Therapeutic, prophylactic or diagnostic compositions of the formulations of the present invention are administered to an individual in amounts sufficient to treat, prevent or diagnose the respective disorder. The effective amount for human administration may, of course, vary according to a variety of factors such as the individual's condition, weight, sex and age. Other factors include the mode of administration. The amount of expressible DNA to be administered to a human recipient will depend on the strength of the transcriptional and translational promoters used in the recombinant viral construct, and, if used as a vaccine, on the immunogenicity of the expressed gene product, as well as the level of pre-existing immunity to a virus such as adenovirus. The formulations of the present invention are optimally a buffered solution. It will be known to one of skill in the art to provide virus formulations of the present invention in a physiologically acceptable buffer, preferably but not necessarily limited to a formulation buffered with Tris (tromethamine), histidine, phosphate, citrate, succinate, acetate, glycine, and borate, within a pH range including but not limited to about 7.0 to about 9.0, preferably a pH range from about 7.5 to about 8.5. Tris is preferred in the exemplified formulations disclosed herein.

An additional aspect of the formulations of the present invention relates to a formulation which comprises a minimal amount of at least one non-ionic surfactant added to reduce adsorption to container surfaces as well as possibly providing increased virus stabilization. Non-ionic surfactants for use in the formulations of the present invention include but are not limited to polyoxyethylene sorbitan fatty acid esters, including but not limited to Polysorbate-80 (Tween 80®), Polysorbate-60 (Tween 60®), Polysorbate-40 (Tween 40®) and Polysorbate-20 (Tween 20®), polyoxyethylene alkyl ethers, including but not limited to Brij 58®, Brij 35®, as well as others such as Triton X-100®, Triton X-114®, NP40®, Span 85 and the Pluronic series of non-ionic surfactants (e.g., Pluronic 121).

An additional component which further stabilizes the added viral component comprise the addition of at least one salt of a divalent cation, including but not necessarily limited to $MgCl_2$, $CaCl_2$ and $MnCl_2$. The preferred divalent cations are $MgCl_2$ and $CaCl_2$ at a concentration ranging from about 0.1 mM to about 5 mM.

Another component which contributes to virus stabilization over large temperature ranges and for prolonged storage periods is a cryoprotectant, especially at concentrations amenable to human administration. Cyroprotectants include but are not necessarily limited to addition of polyhydroxy hydrocarbons such as sorbitol, mannitol, glycerol and dulcitol and/or disaccharides such as sucrose, lactose, maltose or trehalose.

An additional component of the formulations of the present invention which enhance viral stability comprise a salt, including but not necessarily limited to sodium chloride, sodium sulfate, and ammonium sulfate, present at an ionic strength which is physiologically acceptable to the host. A purpose of inclusion of a salt in the formulation is to attain the desired ionic strength or osmolarity. Contributions to ionic strength may come from ions produced by the buffering compound as well as from the ions of non-buffering salts.

A centerpiece of the formulations of the present invention which enhance viral stability relate to inclusion of components that act as inhibitors of free radical oxidation. As noted throughout the specification, virus stability in a pharmaceutical formulation may be effected by the type of buffer, salt concentration, pH, light exposure, temperature storage and the such. It is also shown herein that components which may inhibit free radical oxidation further enhance the stability characteristics of the core adenoviral formulations disclosed herein. Free radical oxidation inhibitors which may be utilized include but are not necessarily limited to ethanol (EtOH), EDTA, an EDTA/ethanol combination, triethanolamine (TEOA), mannitol, histidine, glycerol, sodium citrate, inositol hexaphosphate, tripolyphosphate, succinic and malic acid, desferal, ethylenediamine-Di(o-hydoxy-phenylacetic acid (EDDHA) and diethylenetriaminepenta-acetic acid (DTPA), or specific combinations thereof. It is preferred that the inhibitor of free radical oxidation be either an EDTA/EtOH combination, EtOH alone, or triethanolamine (TEOA). It is shown herein that the combination with other components may determine the effectiveness of the free radical oxidation inhibitor. For example, the combination of EDTA/EtOH is shown to be very effective at increasing stability, while DTPA (alone) in the absence of $MgCl_2$ also enhances stability. Therefore, the skilled artisan may "mix and match" various components, in some cases a scavenger and a chelator are required, while other formulations only a chelator may be required. Preferably, the choice of chelator will determine whether or not the addition of a scavenger is needed. Additional free radical scavengers and chelators are known in the art and apply to the formulations and methods of use described herein. It is disclosed herein that addition of such inhibitors of free radical oxidation results in a substantial increase in long term stability of liquid virus formulations. It is noted that the present invention is not limited to use of these excipients only in the preferred formulations described herein, but are in fact meant to include additional, non-exemplified virus formulations which will be amenable to increased stability within useful temperature ranges by the addition of one or more of these compounds.

The formulations of the present invention which enhance viral stability rely on a useful range of total osmolarity which both promotes long term stability at temperature of 2-8° C., or higher, while also making the formulation useful for parenteral, and especially intramuscular, injection. To this end the effective range of total osmolarity (the total number of molecules in solution) is from about 200 mOs/L to about 800 mOs/L, with a preferred range from about 250 mOs/L to about 450 mOs/L. An especially preferred osmolarity for the formulations disclosed herein is about 300 mOs/L. Therefore, it will be apparent that the amount of a cyroprotectant, such as sucrose or sorbitol, will depend upon the amount of salt in the formulation in order for the total osmolarity of the solution to remain within an appropriate range. Therefore a salt free formulation may contain from about 5% to about 25% sucrose, with a preferred range of sucrose from about 7% to about 15%, with an especially preferred sucrose concentration in a salt free formulation being from 10% to 12%. Alternatively, a salt free sorbitol-based formulation may contain sorbitol within a range from about 3% to about 12%, with a preferred range from about 4% to 7%, and an especially preferred range is from about 5% to about 6% sorbitol in a salt-free formulation. Salt-free formulations will of course warrant increased ranges of the respective cryoprotectant in order to maintain effective osmolarity levels. To again utilize sucrose and sorbitol as examples, and not as a limitation, an effective range of a sucrose-based solution in 75 mM NaCl is from about 2% about 7.5% sucrose, while a sorbitol-based solution in 75 mM NaCl is from about 1% to about 4% sorbitol.

In view of the discussion above, the present invention relates to a formulation containing an adenovirus, such as a recombinant adenovirus for use in gene therapy and/or gene vaccination applications, with show increased viral stability properties and which at least contain a buffer, a salt, a sugar and a surfactant.

A particular embodiment of the present invention relates to such a recombinant adenovirus formulation which comprises Tris as the buffer, sucrose as the cryoprotectant, NaCl as the salt, $MgCl_2$ as the divalent cation and either Polysorbate-80 or Polysorbate-40 as the surfactant.

In a particular embodiment of the present invention the formulation is buffered with Tris to a range from about pH 7.5 to about pH 8.5; sucrose is added within a range upwards of a weight to volume percentage of 10, depending upon the salt concentration; the salt being NaCl which is added at concentration within a range of upwards of 250 mM NaCl, complementing the sucrose concentration such that total osmolarity ranges from about 200 mOs/L to about 800 mOs/L; the divalent cation is $MgCl_2$ in a range from about 0.1 mM to about 10 mM, and the surfactant is either Polysorbate-80 at a concentration from about 0.001% to about 1% or Polysorbate-40 at a concentration from about 0.001% to about 1%.

In a further embodiment of the present invention the formulation is buffered with about 1 mM to about 10 mM Tris to a range from about pH 7.5 to about pH 8.5; sucrose is present in a weight to volume range of about 2% to about 8% and NaCl is present from a range of about 25 mM to about 250 mM, the sucrose and NaCl concentrations being complementary such that the total osmolarity ranges from about 200 mOs/L to about 800 mOs/L; the divalent cation is $MgCl_2$ in a range from about 0.1 mM to about 5 mM, and the surfactant is either Polysorbate-80 at a concentration from about 0.001% to about 0.25% or Polysorbate-40 at a concentration from about 0.001% to 0.25%.

In another embodiment of the present invention the formulation is buffered with about 2.5 mM to about 7.5 mM Tris to a pH of about 8.0; sucrose is present in a weight to volume range of about 2% to about 8% and NaCl is present from a range of about 25 mM to about 250 mM, the sucrose and NaCl contributing to a total osmolarity range from about 250 mOs/L to about 450 mOs/L; the divalent cation is $MgCl_2$ in a range from about 0.5 mM to about 2.5 mM, and the surfactant is either Polysorbate-80 at a concentration from about 0.001% to about 0.1% or Polysorbate-40 at a concentration from about 0.001% to 0.1%.

In a further embodiment of the present invention the formulation is buffered with about 5.0 mM Tris to a pH of about 8.0; sucrose is present in a weight to volume range of about 4% to about 6% and NaCl is present from a range of about 50 mM to about 100 mM, the sucrose and NaCl contributing to a total osmolarity range from about 250 mOs/L to about 450 mOs/L; the divalent cation is $MgCl_2$ in a range from about 1 mM to about 2 mM, and the surfactant is either Polysorbate-80 at a concentration from about 0.001% to about 0.1% or Polysorbate-40 at a concentration from about 0.001% to 0.1%.

In a still further embodiment of the present invention the formulation is buffered with about 5.0 mM Tris, at pH 8.0; sucrose is present in a weight to volume of about 5%; NaCl is present at about 75 mM, with the total osmolarity at about 300 mOs/L; $MgCl_2$ in at about 1 mM to 2 mM, and either Polysorbate-80 is present at a concentration of about 0.02% or Polysorbate-40 at a concentration of about 0.005%.

An exemplified portion of the present invention the formulation is buffered with about 5.0 mM Tris, at pH 8.0; sucrose is present in a weight to volume of 5% (146 mM); NaCl is present at 75 mM, with the total osmolarity approximately 310 mOs/L; $MgCl_2$ at 1 mM, and Polysorbate-80 is present at a concentration of 0.005%. This formulation is herein designated A105.

Another exemplification shows an effective PS-80 range to at least 0.1%, as opposed to A105, where PS-80 is found at 0.005%. This formulation is buffered with about 5.0 mM Tris, at pH 8.0; sucrose is present in a weight to volume of 5% (146 mM); NaCl is present at 75 mM, $MgCl_2$ is at 1 mM, and Polysorbate-80 is present at a concentration of 0.1%. This formulation is herein designated A111.

Another embodiment of the present invention is exemplified by a formulation buffered with about 5.0 mM Tris, at pH 8.0; sucrose is present in a weight to volume of 5% (146 mM); NaCl is present at 75 mM, $MgCl_2$ at 1 mM, and Polysorbate-40 is present at a concentration of 0.005%. This formulation is herein designated A128, as shown in Example 1.

Yet another exemplification is a formulation identical to A128, except that Polysorbate-40 is present at a concentration of 0.1%, showing an effective range of Polysorbate-40. This formulation is herein designated A129, as shown in Example 1.

The present invention further relates recombinant adenovirus formulations which omit at least one component of the above-disclosed component, including but not limited to formulation A108 (no divalent cation) or formulation A109 (no surfactant).

An essential quality of the present invention is the finding that non-reducing free radical scavengers and/or chelators are important for maximizing both short and long term stability of viral formulations, especially recombinant adenoviral formulations disclosed herein. To this end, and as noted above, a critical preferred embodiment of the present invention is a viral formulation which contains one or more components which act as an inhibitor of free radical oxidation. It is shown herein that addition of these components enhance long term stability at temperatures up through the 2-8° C. range, or higher, when compared to core formulations which do not contains these inhibitors. In addition, these formulations are compatible with parenteral administration. The increased stability of these formulations shows that oxidation is a major pathway of adenovirus inactivation which results in a loss of infectivity during storage.

The present invention relates to a recombinant adenoviral formulation buffered with Tris to a range from about pH 7.5 to about pH 8.5; sucrose is added within a range upwards of a weight to volume percentage of 10, depending upon the salt concentration; the salt being NaCl which is added at concentration within a range of upwards of 250 mM NaCl, complementing the sucrose concentration such that total osmolarity ranges from about 200 mOs/L to about 800 mOs/L; the divalent cation is $MgCl_2$ in a range from about 0.1 mM to about 10 mM, and the surfactant is either Polysorbate-80 at a concentration from about 0.001% to about 2% or Polysorbate-40 at a concentration from about 0.001% to about 1%, wherein the formulation further comprises one or more components described herein which inhibit free radical oxidation, including but not limited to ethanol (EtOH), EDTA, an EDTA/ethanol combination, triethanolamine (TEOA), mannitol, histidine, glycerol, sodium citrate, inositol hexaphosphate, tripolyphosphate, succinic and malic acid, desferal, ethylenediamine-Di(o-hydoxy-phenylacetic acid (EDDHA) and diethylenetriaminepenta-acetic acid (DTPA).

In a further embodiment of the present invention the formulation is buffered with about 1 mM to about 10 mM Tris to a range from about pH 7.5 to about pH 8.5; sucrose is present in a weight to volume range of about 2% to about 8% and NaCl is present from a range of about 25 mM to about 250 mM, the sucrose and NaCl concentrations being complementary such that the total osmolarity ranges from about 200 mOs/L to about 800 mOs/L; the divalent cation is $MgCl_2$ in a range from about 0.1 mM to about 5 mM, and the surfactant is either Polysorbate-80 at a concentration from about 0.001% to about 0.25% or Polysorbate-40 at a concentration from about 0.001% to 0.5%, wherein the formulation further comprises one or more components described herein which inhibit free radical oxidation, including but not limited to ethanol (EtOH), EDTA, an EDTA/ethanol combination, triethanolamine (TEOA), mannitol, histidine, glycerol, sodium citrate, inositol hexaphosphate, tripolyphosphate, succinic and malic acid, desferal, ethylenediamine-Di(o-hydoxy-phenylacetic acid (EDDHA) and diethylenetriaminepenta-acetic acid (DTPA).

In a specific embodiment of the present invention the formulation is buffered with about 2.5 mM to about 7.5 mM Tris to a pH of about 8.0; sucrose is present in a weight to volume range of about 2% to about 8% and NaCl is present from a range of about 25 mM to about 250 mM, the sucrose and NaCl contributing to a total osmolarity range from about 250 mOs/L to about 450 mOs/L; the divalent cation is $MgCl_2$ in a range from about 0.5 mM to about 2.5 mM, and the surfactant is either Polysorbate-80 at a concentration from about 0.001% to about 0.1% or Polysorbate-40 at a concentration from about 0.001% to 0.05%, wherein the formulation further comprises one or more components described herein which inhibit free radical oxidation, including but not limited to ethanol (EtOH), EDTA, an EDTA/ethanol combination, triethanolamine (TEOA), mannitol, histidine, glycerol, sodium citrate, inositol hexaphosphate, tripolyphosphate, succinic and malic acid, desferal, ethylenediamine-Di(o-hydoxy-phenylacetic acid (EDDHA) and diethylenetriaminepenta-acetic acid (DTPA).

In another embodiment of the present invention the formulation is buffered with about 5.0 mM Tris to a pH of about 8.0; sucrose is present in a weight to volume range of about 4% to about 6% and NaCl is present from a range of about 50 mM to about 100 mM, the sucrose and NaCl contributing to a total osmolarity range from about 250 mOs/L to about 450 mOs/L; the divalent cation is $MgCl_2$ in a range from about 1 mM to about 2 mM, and the surfactant is either Polysorbate-80 at a concentration from about 0.001% to about 0.1% or Polysorbate-40 at a concentration from about 0.001% to 0.01%, wherein the formulation further comprises one or more components described herein which inhibit free radical oxidation, including but not limited to ethanol (EtOH), EDTA, an EDTA/ethanol combination, triethanolamine (TEOA), mannitol, histidine, glycerol, sodium citrate, inositol hexaphosphate, tripolyphosphate, succinic and malic acid, desferal, ethylenediamine-Di(o-hydoxy-phenylacetic acid (EDDHA) and diethylenetriaminepenta-acetic acid (DTPA).

In a still further embodiment of the present invention the formulation is buffered with about 5.0 mM Tris, at pH 8.0; sucrose is present in a weight to volume of about 5%; NaCl is present at about 75 mM, with the total osmolarity at about 300 mOs/L; $MgCl_2$ in at about 1 mM, and either Polysorbate-80 is present at a concentration of about 0.02% or Polysorbate-40 at a concentration of about 0.005%, wherein the formulation further comprises one or more components described herein which inhibit free radical oxidation, including but not limited to ethanol (EtOH), EDTA, an EDTA/ethanol combination, triethanolamine (TEOA), mannitol, histidine, glycerol, sodium citrate, inositol hexaphosphate, tripolyphosphate, succinic and malic acid, desferal, ethylenediamine-Di(o-hydoxy-phenylacetic acid (EDDHA) and diethylenetriaminepenta-acetic acid (DTPA).

In the above-described formulations, at least one non-reducing free radical scavenger may be added to concentrations which effectively enhance stability of the core formulation. Especially useful ranges include (i) EDTA from about 1 µM to about 500 µM, preferably in a range from about 50

μM to about 250 μM, and an especially preferred concentration of at or around 100 μM; (ii) ethanol from about 0.1% to about 5.0%, preferably in a range from about 0.25% to about 2.0%, and an especially preferred amount totaling at or around 0.5%; (iii) DTPA from about 1 μM to about 500 μM, preferably in a range from about 50 μM to about 250 μM, and an especially preferred concentration at or around 100 μM; (iv) $CaCl_2$ from about 0.1 mM to about 10 mM, preferably in a range from about 0.5 mM to about 5 mM, and an especially preferred concentration at or around 1 mM; and, (v) sodium citrate from about 1 mM to about 100 mM, preferably in a range from about 5 mM to about 25 mM, and an especially preferred concentration at or around 10 mM. These inhibitors of free radical oxidation may also be added in various combinations, including but not limited to two scavengers (e.g., 113), a sole (e.g., A114), or possible a sole scavenger in the absence of another component, such as a divalent cation (e.g., A116).

In another embodiment of the formulation is buffered with about 5.0 mM Tris, at pH 8.0; sucrose is present in a weight to volume of 5% (146 mM); NaCl is present at 75 mM, with the total osmolarity approximately 400 mOs/L; $MgCl_2$ at 1 mM, and Polysorbate-80 is present at a concentration of 0.005%, EDTA is present at 100 μM and ethanol at 0.5%. This formulation is designated A113, as shown in Example 1.

In an additional embodiment the formulation is buffered with about 5.0 mM Tris, at pH 8.0; sucrose is present in a weight to volume of 5% (146 mM); NaCl is present at 75 mM, with the total osmolarity approximately 310 mOs/L; $MgCl_2$ at 1 mM, and Polysorbate-80 is present at a concentration of 0.005%, and triethanolamine (TEOA) is present at 1 mM. This formulation is herein designated A114, as shown in Example 1.

In another embodiment the formulation is buffered with about 5.0 mM Tris, at pH 8.0; sucrose is present in a weight to volume of 5% (146 mM); NaCl is present at 75 mM, with the total osmolarity approximately 350 mOs/L; $MgCl_2$ at 1 mM, and Polysorbate-80 is present at a concentration of 0.005%, and sodium citrate at 10 mM. This formulation is herein designated A115, also as shown in Example 1.

In still another embodiment the formulation is buffered with about 5.0 mM Tris, at pH 8.0; sucrose is present in a weight to volume of 5% (146 mM); NaCl is present at 75 mM, Polysorbate-80 is present at a concentration of 0.005%, and DTPA at 100 μM. This formulation is herein designated A116, also as shown in Example 1.

In another embodiment of the present invention the formulation is buffered with about 5.0 mM Tris-HCl, at pH 8.0; sucrose is present in a weight to volume range of 5% (146 mM); NaCl is present at 75 mM, $MgCl_2$ at 1 mM, and Polysorbate-80 is present at a concentration of 0.005%, and mannitol is present at 3% (w/v). This formulation is herein designated A121.

In yet another embodiment the formulation is buffered with about 5.0 mM Tris, at pH 8.0; sucrose is present in a weight to volume of 5% (146 mM); NaCl is present at 75 mM, $MgCl_2$ at 1 mM, Polysorbate-80 is present at a concentration of 0.005%, and ethanol is present at a concentration of 0.5% (A132) and 1.0% (A134). These two formulations are disclosed in Example 1.

Another embodiment shows a formulation buffered with about 5.0 mM Tris, at pH 8.0; sucrose is present in a weight to volume of 5% (146 mM); NaCl is present at 75 mM, with the total osmolarity approximately 310 mOs/L; $MgCl_2$ at 1 mM, Polysorbate-80 is present at a concentration of 0.005%, and EDTA at 100 μM. This formulation is herein designated A133, also as shown in Example 1.

Another preferred embodiment shows a formulation buffered with about 5.0 mM Tris, at pH 8.0; sucrose is present in a weight to volume of 5% (146 mM); NaCl is present at 75 mM, with the total osmolarity approximately 500 mOs/L; $MgCl_2$ at 1 mM, Polysorbate-80 is present at a concentration of 0.005%, EDTA at 100 μM and ethanol 1.0%. This formulation is herein designated A135, also as shown in Example 1.

In another embodiment of the present invention the formulation is buffered with about 5.0 mM Tris, at pH 8.0; sucrose is present in a weight to volume of 5% (146 mM); NaCl is present at 75 mM, with the total osmolarity approximately 400 mOs/L; $MgCl_2$ at 1 mM, Polysorbate-80 is present at a concentration of 0.1%, EDTA at 100 μM and ethanol 0.5%. This formulation is herein designated A136, also shown in Example 1.

As noted above, it is also within the scope of the present invention to substitute a preferred divalent cation such as $MgCl_2$ with a difference divalent cation, $CaCl_2$. Such a substitution may relate to any of the formulations disclosed herein. An example of such a substitution is formulation A120, which comprises 5.0 mM Tris-HCl, at pH 8.0; sucrose is present in a weight to volume of 5% (146 mM); NaCl is present at 75 mM, Polysorbate-80 at 0.005%, EDTA at 100 μM, ethanol at 0.5% and $CaCl_2$ at 1 mM. Formulation A120 is shown in Example 1.

The present invention further relates recombinant adenovirus formulations which omit at least one component of the above-disclosed components, including but not limited to formulation A116 (excipient: DTPA at 100 μM; no divalent cation), formulation A117 (excipients: EDTA at 100 μM and EtOH at 0.5%; no divalent cation), formulation A118 (triethanolamine at 1.0 mM; no divalent cation), formulation A119 (excipient: sodium citrate at 10 mM; no divalent cation).

In addition to the above-disclosed excipients which act as inhibitor of free radical oxidation, the present invention further relates to a recombinant viral formulation which additionally comprises plasmid DNA at a concentration from about 0.01 mg/ml to about 10 mg/ml. The addition of plasmid DNA effectively increases the stability of a recombinant virus formulation, such as the recombinant adenovirus exemplified herein. Therefore, plasmid DNA may be added to any core formulations (e.g., A105 and A128, which do not contain additional excipients such as free radical oxidation inhibitors), as well as core formulations comprising such excipients. A preferred concentration range for the plasmid DNA is from about 0.5 mg/l to about 5.0 mg/ml, with an additionally preferred plasmid DNA concentration at 1 mg/ml.

In another embodiment of the present invention the formulation is buffered with about 5.0 mM Tris-HCl, at pH 8.0; sucrose is present in a weight to volume range of 5% (146 mM); NaCl is present at 75 mM, $MgCl_2$ at 1 mM, and Polysorbate-80 is present at a concentration of 0.005%, and plasmid DNA is present at 0.1 mg/ml. This formulation is herein designated A137.

In still another embodiment of the present invention the formulation is buffered with about 5.0 mM Tris, at pH 8.0; sucrose is present in a weight to volume of 5% (146 mM); NaCl is present at 75 mM, with the total osmolarity approximately 400 mOs/L; $MgCl_2$ at 1 mM, and Polysorbate-80 is present at a concentration of 0.005%, EDTA is present at 100

µM, ethanol is present at 0.5% and plasmid DNA is present at 1 mg/mL. This formulation is designated A138, as shown in Example 1.

In another preferred embodiment of the present invention the formulation is buffered with about 5.0 mM Tris, at pH 8.0; mannitol is present in a weight to volume of 2.7% (147 mM); NaCl is present at 75 mM, with the total osmolarity approximately 400 mOs/L; $MgCl_2$ at 1 mM, and Polysorbate-80 is present at a concentration of 0.005%, EDTA is present at 100 µM and ethanol at 0.5%. This formulation is designated A149, as shown in Example 1.

Another embodiment shows a formulation buffered with about 5.0 mM Tris, at pH 8.0; sucrose is present in a weight to volume of 5% (146 mM); NaCl is present at 75 mM, with the total osmolarity approximately 400 mOs/L; $MgCl_2$ at 1 mM, and Polysorbate-80 is present at a concentration of 0.005%, EDTA is present at 100 µM, ethanol is present at 0.5% and histidine is present at 5 mM. This formulation is designated A151a, as shown in Example 1.

Another embodiment of the present invention disclosed a formulation buffered with about 5.0 mM Tris, at pH 7.5 at 30° C.; while sucrose is present in a weight to volume of 5% (146 mM); NaCl is present at 75 mM, with the total osmolarity approximately 400 mOs/L; $MgCl_2$ at 1 mM, and Polysorbate-80 is present at a concentration of 0.005%, EDTA is present at 100 µM, ethanol is present at 0.5% and histidine is present at 5 mM. This formulation is designated A151b, as shown in Example 1.

In another embodiment of the present invention the formulation is buffered with about 5.0 mM Tris, at pH 7.5 at 30° C.; sucrose is present in a weight to volume of 5% (146 mM); NaCl is present at 75 mM, with the total osmolarity approximately 400 mOs/L; $MgCl_2$ at 2 mM, and Polysorbate-80 is present at a concentration of 0.005%, EDTA is present at 100 µM, ethanol is present at 0.5%, histidine is present at 5 mM and triethanolamine is present at 5 mM. This formulation is designated A152, as shown in Example 1.

In still another embodiment of the present invention the formulation is buffered with about 5.0 mM Tris, at pH 7.5 at 30° C.; sucrose is present in a weight to volume of 5% (146 mM); NaCl is present at 75 mM, with the total osmolarity approximately 400 mOs/L; $MgCl_2$ at 2 mM, and Polysorbate-80 is present at a concentration of 0.005%, EDTA is present at 100 µM, ethanol is present at 0.5%, histidine is present at 5 mM, triethanolamine is present at 5 mM and glycerol is present at 5% (v/v). This formulation is designated A153, as shown in Example 1.

As noted above, the dosage regimen utilizing the compounds of the present invention is selected in accordance with a variety of factors including type, level of pre-existing immunity to adenovirus, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The formulated recombinant viruses described herein may also be formulated with an adjuvant or adjuvants which may increase immunogenicity of the expressed transgene. A number of these adjuvants are known in the art and are available for use, including but not limited to saponin, monophosphoryl lipid A, non-ionic block copolymers composed of polyoxyethylene and polyoxypropylene or other compounds which increase immunogenicity of expressed transgene. Another adjuvant for use with the recombinant viruses described herein are one or more forms of an aluminum phosphate-based adjuvant wherein the aluminum phosphate-based adjuvant possesses a molar $PO_4$/Al ratio of approximately 0.9. An additional mineral-based adjuvant may be generated from one or more forms of a calcium phosphate. These mineral-based compounds for use as DNA vaccines adjuvants are disclosed in PCT International Application No. PCT/US98/02414 (WO 98/35562), which is hereby incorporated by reference.

The recombinant virus formulations described herein are administered to the vertebrate host (preferably a mammalian host and especially a human recipient) by any means known in the art, such as enteral and parenteral routes. These routes of delivery include but are not limited to intramusclar injection, intraperitoneal injection, intravenous injection, inhalation or intranasal delivery, oral delivery, sublingual administration, subcutaneous administration, transdermal administration, transcutaneous administration, percutaneous administration or any form of particle bombardment, such as a biolostic device such as a "gene gun" or by any available needle-free injection device. The preferred methods of delivery of the recombinant viruses described herein are intramuscular injection and needle-free injection. An especially preferred method is intramuscular delivery.

In accordance with the formulation compositions disclosed herein, the present invention also relates to methods of stabilizing virus formulation which comprises generating virus-containing formulations disclosed herein, such formulations which result in improved viral stability when stored in about the 2-8° C. range and higher while also being compatible with parenteral administration, especially patenteral administration to humans. Therefore, these prescribed methods relate to the disclosed, and especially, the exemplified virus-containing formulations of the present invention. In addition, the present invention relates to a method of stabilizing a virus formulation which comprises adding at least one inhibitor of free radical oxidation to the formulation, such that the resultant formulation shows improved stability in about the 2-8° C. range and higher while also being compatible with parenteral administration. Also, the present invention relates to a method of stabilizing a virus formulation which comprises adding a nucleic acid to the formulation, such that the resultant formulation also shows improved stability in about the 2-8° C. range and higher while also being compatible with parenteral administration. Therefore, the present invention relates to a method of stabilizing a virus formulation which comprises preserving the virus of interest, preferably a recombinant virus, in any of the formulations described herein, and especially methods which comprise preservation of the virus by addition of at least one one inhibitor of free radical oxidation and/or addition a nucleic acid to the formulation, such that the resultant formulation also shows improved stability in about the 2-8° C. range and higher while also being compatible with parenteral administration.

The following examples are provided to illustrate the present invention without, however, limiting the same hereto.

Materials—Adenovirus type 5 containing the FL HIV-gag transgene (Ad5gag) was used for these experiments. This Ad5FLHIVgag recombinant virus is described in detail in U.S. Provisional Application 60/148,981, filed Aug. 13, 1999, which is hereby incorporated by reference. The recombinant Ad5gag virus was purified by column chromatography.

Methods:

1. TCID50 Adenovirus Infectivity Assay: The $TCID_{50}$ assay is a method for titrating the infectivity of adenovirus, using a $TCID_{50}$ end-point dilution method in a 96-well format. Cells in each well of the 96-well plate that are infected with adenovirus are revealed using a vital staining method based on the Tetrazolium dye (MTS). The amount of color formation per well is correlated with the quantity of living cells, which reflects the extent of adenovirus replication.

2. QPA Adenovirus Infectivity Assay—The QPA assay is a procedure for the rapid quantitation of adenovirus infectivity based on the use of Q-PCR technology to quantitate accumulated adenoviral genomes 24 hours after infection of cells.

The following examples are provided to illustrate the present invention without, however, limiting the same hereto.

EXAMPLE 1

Exemplified Formulation Number and Components

Formulation numbers represent exemplified formulations which, along with accompanying stability data, support the claims appended hereto.

| Form. # | Description |
| --- | --- |
| A101 | 10 mM Tris, 10% glycerol (v/v), 1 mM $MgCl_2$, pH 7.5 |
| A102 | 6 mM phosphate, 150 mM NaCl, 10% glycerol (v/v), pH 7.2 |
| A103 | 6 mM phosphate, 150 mM NaCl, pH 7.2 |
| A104 | 5 mM Tris, 150 mM NaCl, 1 mM $MgCl_2$, 0.005% PS-80, pH 8.0 |
| A105 | 5 mM Tris, 75 mM NaCl, 5% sucrose (w/v), 1 mM $MgCl_2$, 0.005% PS-80, pH 8.0 |
| A106 | 5 mM Tris, 14% sucrose (w/v), 1 mM $MgCl_2$, 0.005% PS-80, pH 8.0 |
| A107 | 5 mM Tris, 8% sorbitol (w/v), 1 mM $MgCl_2$, 0.005% PS-80, pH 8.0 |
| A108 | 5 mM Tris, 75 mM NaCl, 5% sucrose (w/v), 0.005% PS-80, pH 8.0 |
| A109 | 5 mM Tris, 75 mM NaCl, 5% sucrose (w/v), 1 mM $MgCl_2$, pH 8.0 |
| A110 | 5 mM Tris, 75 mM NaCl, 5% sucrose (w/v), 1 mM $MgCl_2$, 0.02 PS-80, pH 8.0 |
| A111 | 5 mM Tris, 75 mM NaCl, 5% sucrose (w/v), 1 mM $MgCl_2$, 0.1% PS-80, pH 8.0 |
| A112 | 5 mM Tris, 75 mM NaCl, 5% sucrose (w/v), 1 mM $MgCl_2$, 0.005% PS-80, 100 μm DTPA, pH 8.0. |
| A113 | 5 mM Tris, 75 mM NaCl, 5% sucrose (w/v), 1 mM $MgCl_2$, 0.005% PS-80, 100 μM EDTA, 0.5% EtOH, pH 8.0 |
| A114 | 5 mM Tris, 75 mM NaCl, 5% sucrose (w/v), 1 mM $MgCl_2$, 0.005% PS-80, 1.0 mM TEOA, pH 8.0 |
| A115 | 5 mM Tris, 75 mM NaCl, 5% sucrose (w/v), 1 mM $MgCl_2$, 0.005% PS-80, 10 mM sodium citrate, pH 8.0 |
| A116 | 5 mM Tris, 75 mM NaCl, 5% sucrose (w/v), 0.005% PS-80, 100 μM DTPA, pH 8.0 |
| A117 | 5 mM Tris, 75 mM NaCl, 5% sucrose (w/v), 0.005% PS-80, 100 μM EDTA, 0.5% EtOH, pH 8.0 |
| A118 | 5 mM Tris, 75 mM NaCl, 5% sucrose (w/v), 0.005% PS-80, 1.0 mM TEOA, pH 8.0 |
| A119 | 5 mM Tris, 75 mM NaCl, 5% sucrose (w/v), 0.005% PS-80, 10 mM sodium citrate, pH 8.0 |
| A120 | 5 mM Tris, 75 mM NaCl, 5% sucrose (w/v), 0.005% PS-80, 100 μM EDTA, 0.5% EtOH, 1 mM $CaCl_2$, pH 8.0 |
| A121 | 5 mM Tris, 5% sucrose (w/v), 1 mM $MgCl_2$, 3% (w/v) mannitol, 0.005% PS-80, pH 8.0 |
| A125 | 5 mM Tris, 75 mM NaCl, 5% sucrose (w/v), 1 mM $MgCl_2$,, 10 mM ascorbic acid, 0.005% PS-80, pH 8.0 |
| A126 | 5 mM Tris, 75 mM NaCl, 5% sucrose (w/v), 1 mM $MgCl_2$, 0.05% PS-80, pH 8.0 |
| A127 | 5 mM Tris, 75 mM NaCl, 5% sucrose (w/v), 1 mM $MgCl_2$, 0.15% PS-80, pH 8.0 |
| A128 | 5 mM Tris, 75 mM NaCl, 5% sucrose (w/v), 1 mM $MgCl_2$, 0.005% PS-40, pH 8.0 |
| A129 | 5 mM Tris, 75 mM NaCl, 5% sucrose (w/v), 1 mM $MgCl_2$, 0.1% PS-40, pH 8.0 |
| A130 | 5 mM Tris, 75 mM NaCl, 5% sucrose (w/v), 2 mM $MgCl_2$, 0.005% PS-80, pH 8.0 |
| A131 | 5 mM Tris, 75 mM NaCl, 5% sucrose (w/v), 5 mM $MgCl_2$, 0.005% PS-80, pH 8.0 |
| A132 | 5 mM Tris, 75 mM NaCl, 5% sucrose (w/v), 1 mM $MgCl_2$, 0.005% PS-80, 0.5% EtOH, pH 8.0 |
| A133 | 5 mM Tris, 75 mM NaCl, 5% sucrose (w/v), 1 mM $MgCl_2$, 0.005% PS-80, 100 μM EDTA, pH 8.0 |
| A134 | 5 mM Tris, 75 mM NaCl, 5% sucrose (w/v), 1 mM $MgCl_2$, 0.005% PS-80, 1.0% EtOH, pH 8.0 |
| A135 | 5 mM Tris, 75 mM NaCl, 5% sucrose (w/v), 1 mM $MgCl_2$, 0.005% PS-80, 100 μM EDTA, 1.0% EtOH, pH 8.0 |
| A136 | 5 mM Tris, 75 mM NaCl, 5% sucrose (w/v), 1 mM $MgCl_2$, 0.1% PS-80, 100 μM EDTA, 0.5% EtOH, pH 8.0 |
| A137 | 5 mM Tris, 75 mM NaCl, 5% sucrose (w/v), 1 mM $MgCl_2$, 0.005% PS-80, 1 mg/ml plasmid DNA comprising an HIV-1 gag sequence, pH 8.0 A138 |
| A138 | 5 mM Tris, 75 mM NaCl, 5% sucrose (w/v), 1 mM $MgCl_2$, 0.005% PS-80, 100 μM EDTA, 0.5% EtOH, 1 mg/ml plasmid DNA comprising an HIV-1 gag sequence, pH 8.0 |
| A149 | 5 mM Tris, 75 mM NaCl, 2.7% (w/v) mannitol, 1 mM $MgCl_2$, 0.005% PS-80, 100 μM EDTA, 0.5% EtOH, pH 8.0 |
| A151a | 5 mM Tris, 75 mM NaCl, 5% sucrose (w/v), 1 mM $MgCl_2$, 0.005% PS-80, 100 μM EDTA, 0.5% EtOH, 5 mM histidine, pH 8.0 |
| A151b | 5 mM Tris, 75 mM NaCl, 5% sucrose (w/v), 1 mM $MgCl_2$, 0.005% PS-80, 100 μM EDTA, 0.5% EtOH, 5 mM histidine, pH 7.5 at 30° C. |
| A152 | 5 mM Tris, 75 mM NaCl, 5% sucrose (w/v), 2 mM $MgCl_2$, 0.1% PS-80, 100 μM EDTA, 0.5% EtOH, 5 mM histidine, 5 mM TEOA, pH 7.5 at 30° C. |
| A153 | 5 mM Tris, 75 mM NaCl, 5% sucrose (w/v), 2 mM $MgCl_2$, 0.1% PS-80, 100 μM EDTA, 0.5% EtOH, 5 mM histidine, 5 mM TEOA, 5% (v/v) glycerol, pH 7.5 at 30° C. |
| A155 | 15 mM Tris, 75 mM NaCl, 5% sucrose (w/v), 1 mM $MgCl_2$, 0.005% PS-80, 100 μM EDTA, 0.5% EtOH, pH 8.0 |

-continued

| Form. # | Description |
| --- | --- |
| A159 | 5 mM Tris, 75 mM NaCl, 2.7% mannitol (w/v), 1 mM MgCl$_2$, 0.005% PS-80, 100 µM EDTA, 0.5% EtOH, 5 mM histidine, pH 8.0 |
| A160 | 5 mM Tris, 75 mM NaCl, 2.7% mannitol (w/v), 1 mM MgCl$_2$, 0.005% PS-80, 100 µM EDTA, 5 mM histidine, pH 8.0 |
| A165 | 5 mM Tris, 75 mM NaCl, 5% sucrose (w/v), 2 mM MgCl$_2$, 0.1% PS-80, 100 µM EDTA, 0.5% EtOH, 5 mM histidine, pH 7.5 at 30° C. |
| A166 | 10 mM Tris, 75 mM NaCl, 5% sucrose (w/v), 1 mM MgCl$_2$, 0.1% PS-80, 100 µM EDTA, 0.5% EtOH, 7.5 mM histidine, 1 mM TEOA, pH 7.6 |
| A167 | 10 mM Tris, 75 mM NaCl, 5% sucrose (w/v), 1 mM MgCl$_2$, 0.1% PS-80, 100 µM EDTA, 0.5% EtOH, 10 mM histidine, 1 mM TEOA, pH 8.0 |
| A168 | 10 mM Tris, 75 mM NaCl, 5% sucrose (w/v), 1 mM MgCl$_2$, 0.1% PS-80, 100 µM EDTA, 0.5% EtOH, 7.5 mM histidine, 1 mM TEOA, 1.0% mannitol, pH 7.7 |
| A169 | 10 mM Tris, 75 mM NaCl, 5% sucrose (w/v), 1 mM MgCl$_2$, 0.1% PS-80, 100 µM EDTA, 0.5% EtOH, 10 mM histidine, 1 mM TEOA, 1% mannitol, pH 8.0 |
| A170 | 10 mM Tris, 75 mM NaCl, 5% sucrose (w/v), 1 mM MgCl$_2$, 0.1% PS-80, 100 µM EDTA, 0.5% EtOH, 10 mM histidine, pH 8.0 |
| A171 | 10 mM Tris, 75 mM NaCl, 5% sucrose (w/v), 0.1% PS-80, 100 µM EDTA, 0.5% EtOH, 10 mM histidine, 1 mM TEOA, 1% mannitol, pH 8.0 |
| A172 | 10 mM Tris, 75 mM NaCl, 5% sucrose (w/v), 0.005% PS-80, 100 µM EDTA, 0.5% EtOH, pH 8.0 |
| A173 | 10 mM Tris, 75 mM NaCl, 5% sucrose (w/v), 0.005% PS-80, 100 µM EDTA, 0.5% EtOH, 10 mM histidine, pH 8.0 |

EXAMPLE 2

Effect of Freeze/Thaw on the Recovery and Stability of Human Adenovirus 5

The effect of freeze/thaw on the recovery/stability of Ad5gag was examined initially in formulations A101-A107 at both $10^7$ and $10^9$ vp/mL. FIG. 1 shows the effects of one freeze/thaw cycle (from −70° C. to 5° C.) on the recovery/stability of Ad5gag in the initial seven formulations, as measured by the QPA assay. The results indicate that Ad5gag lost significant amounts of infectivity, or was adsorbed to the glass vial, in the two formulations that did not contain a cryoprotectant (A103 and A104). The results also indicated that the infectivity was at the level expected for the Ad5gag concentration in A101, A102, A105-A107, suggesting that there was no significant loss of recovery from the glass vial. The effects of multiple freeze/thaw cycles were also examined. The data in FIG. 2 show the effects of 1 to 3 freeze/thaw cycles on the recovery/stability of Ad5gag in the initial formulations. The results indicated severe losses in infectivity, or adsorption to the glass vial, for Ad5gag in A103 and A104 and suggested some loss of infectivity for A106 and A107 after 2-3 freeze/thaw cycles.

To confirm the loss of infectivity in A103 and A104 after freeze/thaw and to determine the efficiency of recovering Ad5gag from the final containers, the TCID$_{50}$ assay was performed on Ad5gag in the initial formulations after one freeze/thaw cycle. The results, shown in FIG. 3, indicate large losses in infectivity/recovery for Ad5gag in A103 and A104, but with no significant infectivity losses observed for Ad5gag in the other formulations. The results also indicated no significant loss of recoverable Ad5gag from the glass containers or the other formulations, since the ratio of VP/IU was in the expected range of ~20, based on TCID$_{50}$ assays of the same lot of Ad5gag that was not stored in glass vials.

Additional freeze/thaw studies were done with Ad5gag in A105 since the results of the early freeze/thaw and stability data suggested that Ad5gag was more stable in A105 than the other initial formulations. The data in FIG. 4 show the effect of 12 freeze/thaw cycles on the stability of Ad5gag in A105 at $10^8$, $10^{10}$ and $10^{11}$ vp/mL. The results indicate that Ad5gag in A105 was stable through 12 freeze/thaw cycles and after 4 freeze/thaw cycles followed by 8.5 hours at 2-8° C.

A freeze/thaw study was also performed to determine the effect of freezing and thawing a large aliquot of Ad5gag in A105, to simulate the handling of clinical bulks prior to filling. For this experiment 600 mL of Ad5gag in A105 at $10^8$ vp/mL was frozen at −70° C. The sample was then thawed at 2-8° C. and assayed for infectivity by QPA. Following 51.5 hours of thawing at 2-8° C. the aliquot was incubated further at 15° C. for 20 hours, to simulate handling of clinical materials during a filling operation, then assayed again. The results shown in FIG. 5 indicate that the freezing, thawing and 15° C. incubation did not have a significant affect on the infectivity of Ad5gag in A105.

EXAMPLE 3

Evaluation of Human Adenovirus Formulations Based on Short-Term Stability

One of the initial stability studies was designed to test the short-term stability of Ad5gag in the candidate formulations at 2-8° C. Since one of the stability criteria for implementation into a GMP clinical supplies operation was to ensure stability through a filling operation, a short-term study was initiated using Ad5gag at both $10^7$ and $10^9$ vp/mL in 3 mL glass vials, and assaying for infectivity by QPA after 72 hours of storage at 2-8° C. The results in FIG. 6 indicate that Ad5gag in formulation A102 was significantly less stable than in the other formulations tested. These QPA results were obtained by measuring the log loss in infectivity compared to the −70° C. control.

The stability of Ad5gag in A102, A105, A106 and A107 was also determined at both $10^7$ and $10^9$ vp/mL by QPA after 6 months of storage at −15° C. The results indicated <0.1 log loss of infectivity in formulations A105, A106 and A107 but 0.27 log loss for Ad5gag in A102, at each concentration, compared to a −70° C. control. TCID$_{50}$ assays conducted after 6 months of storage at −15° C. ($10^9$ vp/mL) indicated that Ad5gag in formulation A102 lost 0.6 logs of infectivity, while there was <0.1 log loss in formulations A105, A106 and A107. Additional short-term stability studies were conducted at 2-8, 15, 25 and 37° C. to compare the stability of Ad5gag in A105, A106 and A107 (compared to a −70° C. control). These studies were done with Ad5gag at $10^7$ vp/mL with timepoints at 1, 2 3 and 4 weeks at 2-8, 15 and 25° C. The stability at 37° C. was determined at 3, 7, 10 and 14 days. The 2-8° C. data shown in FIG. 7 suggested that Ad5gag in A105 is more stable than in either A106 or A107.

The 15, 25 and 37° C. stability data are shown in FIGS. 8, 9 and 10, respectively. These results clearly indicate that Ad5gag in A105 is significantly more stable than in A106 or A107.

EXAMPLE 4

Effect of pH on the Stability of Human Adenovirus 5

The effect of pH on the stability of Ad5gag has been examined in a number of experiments. One experiment was designed to determine the activation energy for Ad5gag inactivation at two different pH values. For this experiment Ad5gag was formulated in a buffer containing 75 mM NaCl, 5% sucrose, 1 mM $MgCl_2$, 0.005% PS-80 and either 20 mM Tris or 20 mM Bis-tris-propane as the buffer. The Tris buffered solutions were adjusted to pH 8.6 at each temperature (37, 30, 25 and 15° C.) while the Bis-tris-propane buffered formulations were adjusted to pH 7.4. The results, shown in FIG. 11 suggest that there are different inactivation mechanisms predominating at pH 7.4 and pH 8.6. Moreover, the results preliminarily suggest that the major inactivation pathway is different above and below 15° C. and that the optimum pH for Ad5gag stability is different above and below 15° C. Based on these data the activation energies for the pH 8.6 and pH 7.4 inactivation pathways are 34 and 19 kcal/mol, respectively.

The data in FIG. 11 suggest that below 15° C. the pH 7.4 pathway is the major inactivation pathway. Therefore, it seems possible that below 15° C. even a formulation at pH 8.6 would be inactivated at a rate consistent with the pH 7.4 pathway. Data from another experiment has been included in FIG. 11 to show the rate of inactivation of Ad5gag in A105 at both 15 and 5° C. The results suggest that the rate of Ad5gag inactivation in A105 (which is pH 8.6 at 5° C.) is consistent with the pH 7.4 pathway predominating below 15° C. These data suggest that to develop Ad5gag formulations more stable than A105 at 2-8° C. it will be necessary to reduce the rate of the pH 7.4 inactivation pathway.

In another experiment the effect of pH on the stability of Ad5gag was examined after 3 months of storage at 2-8, 15 and 25° C. The results, shown in FIG. 12, are consistent with the Arrhenius data in FIG. 11 indicating that the pH for optimum stability is different above and below 15° C. At 2-8° C. the optimum pH appears to be in the range of 8.0 to 9.0, with a maximum at pH 8.5. At 25° C. the pH for optimum stability is in the range of 7.0 to 7.5. Also noted in this experiment was an extreme loss of infectivity for the pH 7.0 formulation at 2-8° C. Because the −70° C. control for the 2-8° C. samples also lost ~2 logs of infectivity it was clear that the 2-8° C. storage was not totally responsible for the lost infectivity. Moreover, the −70° C. control for the pH 7.0 formulations to be stored at 15° C. also lost infectivity (~0.3 logs). It seem likely that the loss of infectivity was due to the brief exposure to a pH lower than 7.0 during the time the pH 7.0 formulations were near 25° C. Since these formulations contain Tris there is a relatively large pH change with temperature. Therefore, the pH 7.0 formulations prepared for storage at 2-8° C. and 15° C. were adjusted to pH 6.5 and 6.75 at 25° C., respectively. These data suggest that Ad5gag is very unstable below pH 7.0.

The effect of pH on the long-term stability of Ad5gag was also examined after 12 months of storage at 15° C. and 25° C. The results, shown in FIG. 13, are consistent with the data shown in FIG. 12 and indicate that the pH of optimum stability for Ad5gag is ~pH 7.5 at 15° C. and is ~pH 7.0 to 7.5 at 25° C.

The effect of pH on the long-term stability of Ad5gag at 2-8° C. is shown in FIG. 14. Based on 12 months of stability data the optimum pH for Ad5gag stability was found to be between 8.0 and 8.5, at 2-8° C.

EXAMPLE 5

Effect of $MgCl_2$ on the Stability of Human Adenovirus 5

The effect of $MgCl_2$ on the stability of Ad5gag has been examined in two experiments. In the first experiment the stability of Ad5gag was compared in A105 and A108 to determine whether $MgCl_2$ was necessary for Ad5gag stability. The results, shown in FIG. 15, clearly indicate that $MgCl_2$ is necessary for optimum Ad5gag stability in A105.

In the second experiment the effect of 1, 2 and 5 mM $MgCl_2$ on the stability of Ad5gag was compared at 30° C. The results shown in FIG. 16 suggest that the optimum $MgCl_2$ concentration for maximum Ad5gag stability is 2 mM, at this pH and temperature.

EXAMPLE 6

Effect of Polysorbate on the Stability of Human Adenovirus 5

The effect of polysorbate-80 (PS-80) on the stability of Ad5gag is shown in FIG. 17. It is clear from the data that polysorbate is necessary for optimum Ad5gag stability over a wide range of temperatures.

The results of the first experiment to examine the effect of PS-80 concentration on Ad5gag stability is shown in FIG. 18 above. The results strongly suggest that PS-80 concentrations higher than the 0.005% are necessary for optimum Ad5gag stability in A105.

In another experiment to examine the effect of PS-80 the concentration was varied from 0.005% to 0.15%, as shown above in FIG. 19. The results from the accelerated stability studies at 25 and 30° C. suggested that 0.1% PS-80 is the optimum concentration for maximum stability. However, the optimum PS-80 concentration may be different at lower temperatures (ongoing studies).

The effect of polysorbate type on Ad5gag stability has also been examined. The data shown in FIG. 20 above show a comparison of the Ad5gag stability in formulations containing either PS-80 or PS-40 at two concentrations. PS-40 was chosen because it lacks unsaturation and is more stable to oxidation than PS-80. The results at 25° C. indicate that Ad5gag was more stable in the PS-40 containing formulations than in the equivalent PS-80 formulation. The 30° C. results indicated that Ad5gag was more stable with PS-40 at 0.005% but less stable at 0.1%. These data suggest that PS-40 provides some stability advantage over PS-80 at 25° C. or lower.

EXAMPLE 7

Effect of Adenovirus Concentration on the Storage Stability at 37° C., in A105

Ad5gag was formulated at $10^9$ and $10^{11}$ vp/mL in A105 and placed on stability at 37° C. Infectivity was determined after 3, 7, 10, 14 and 21 days. The results, shown in FIG. 21, clearly indicate that Ad5gag concentration did not have a significant effect of stability at 37° C.

The data in FIGS. 24-26 (discussed in Example 10 below) also show no effect of Ad5gag concentration on stability at −70° C. and −15° C., between $10^7$ and $10^{11}$ vp/mL.

EXAMPLE 8

Enhancement of Adenovirus Stability by Inhibitors of Free Radical Oxidation

The first experiment to test the susceptibility of Ad5gag to free radical oxidation was designed to explore the effects of ascorbic acid and trace amounts of $Fe^{+2}$ and $Fe^{+3}$ added to A105. Since ascorbic acid is a potent accelerator for free radical oxidation catalyzed by trace metal ions we reasoned that ascorbic acid would quickly inactivate Ad5gag if it were sensitive to free radical oxidation. We also tested the effects of added $Fe^{+2}$ and $Fe^{+3}$ since they also might be expected to increase the rate of free radical oxidation. Fe+2 in particular is a very potent accelerator for hydroxyl radical production from hydrogen peroxide. The results, shown in FIG. 22, clearly indicate that Ad5gag is very susceptible to free radical oxidation induced by both ascorbic acid (in A125) and iron. These results also suggested that it was likely that free radical oxidation may be a major mechanism of inactivation for Ad5gag in A105.

To determine whether free radical oxidation is a major pathway for inactivation of Ad5gag four different inhibitors of free radical oxidation were tested at three different storage temperatures. The results, shown in FIG. 23, indicate that each free radical inhibitor enhanced the stability of Ad5gag, at each storage temperature. These results strongly suggest that free radical oxidation is a major pathway of Ad5gag inactivation over a wide range of temperatures.

EXAMPLE 9

Effect of Formulation on Lot to Lot Variability in Ad5gag Stability

The stability of Ad5gag was evaluated in eight different lots and in three different formulations (A105, A111 and A113) after one month of storage at 30° C. The data shown below in Table 1 indicate that there was significant variability in the stability of Ad5gag from different lots, in formulations A105 and A111. However, the data also show that the stability of each lot of Ad5gag was improved in formulation A113 compared to A105 or A111 and that the variability was also reduced. These data suggest that variations in the rate of free radical oxidation is a major source of the stability variations seen from lot to lot of Ad5gag.

TABLE 1

Effect of Formulation on lot to lot variability in the stability of Ad5gag*

| Ad5gag lot | Log loss of infectivity after one month at 30° C. vs −70° C. control in:** | | |
|---|---|---|---|
| | A105 | A111 | A113 |
| 1 | 0.91 | 0.94 | 0.55 |
| 2 | 0.75 | 0.69 | 0.20 |
| 3 | 0.62 | 0.60 | 0.26 |
| 4 | 0.53 | 0.60 | 0.23 |
| 5 | 0.56 | 1.09 | 0.30 |
| 6 | 0.51 | 0.63 | 0.27 |
| 7 | 0.95 | 1.07 | 0.28 |
| 8 | 0.68 | 0.80 | 0.34 |

*Ad5gag concentration was $1.0 \times 10^8$ vp/mL
**Loss of infectivity was determined by QPA assay.

EXAMPLE 10

Leading Human Adenovirus 5 Formulations Based on Accelerated and Real-Time Stability Data Based on 6 month stability data Ad5gag in A105 is an acceptable frozen liquid formulation for storage at either −70° C. or −15° C. (see FIG. 24). Moreover, the stability of Ad5gag in A105 is higher than in any of the other initial candidate formulations (A102-A104, A106, A107). The loss of Ad5gag infectivity in A105 at 2-8° C. will be approximately 0.37-0.44 logs/year, suggesting that further improvements in recombinant adenovirus stability are warranted.

Table 1 shows the estimated rate of infectivity loss of exemplified adenoviral formulations. The rate of infectivity loss of various formulations is shown, based on 6 months of stability data at both 2-8° C. and 15° C. Although the 2-8° C. stability data was generated at the intended storage condition the infectivity losses were very small and difficult to measure accurately. Therefore, the rate of infectivity loss was also estimated from an extrapolation of the 15° C. stability data and the activation energy for Ad5gag inactivation using the pH 7.4 pathway (the most conservative extrapolation). The slope of the Arrhenius plot for the pH 7.4 inactivation pathway (see FIG. 11) suggests that Ad5gag should have a shelf life 3.3 times as long at 5° C. as it does at 15° C.

TABLE 2

| Ad5gag formulation | Estimated rate of infectivity loss (logs/year) (based on 6 month 2-8° C. data) | Estimated rate of infectivity loss (logs/year) (based on 6 month 15° C. data) |
|---|---|---|
| A105 | 0.37 | 0.44 |
| A111 | 0.14 | 0.18 |
| A113 | <0.1 | 0.14 |
| A114 | <0.1 | 0.28 |
| A115 | 0.14 | 0.36 |
| A116 | <0.1 | 0.14 |
| A117 | <0.1 | 0.19 |
| A120 | <0.1 | 0.13 |

EXAMPLE 11

Effects of EDTA/EtOH and PS-80 Concentration on the Stability of Human Adenovirus 5

The observation that free radical oxidation is a major mechanism of Ad5gag inactivation during storage has paved the way for the design of additional Ad5gag formulations much more stable than Ad5gag in A105. As shown above, a formulation containing 100 μM EDTA and 0.5% ethanol in an A105 base (A113) shows enhanced stability at 2-8° C. and is an especially preferred formulation of the present invention.

It should be noted that only one formulation lacking free radical oxidation inhibitors provides nearly the same degree of stabilization to Ad5gag as do the formulations containing the inhibitors. This formulation (A111) contains 0.1% PS-80, but is otherwise the same as A105. These results suggest that optimization of the polysorbate type and concentration is also very important to maximum Ad5gag stability and also suggests that polysorbate may be affecting a different inactivation pathway than the oxidation inhibitors. Therefore, combining 0.1% PS-80 and EDTA/EtOH in a single formulation (A136) may possibly inhibit two different inactivation pathways. The results in FIG. 27 show data to test this hypothesis. The results indicate that the stability enhancing effects of 0.1% PS-80 and EDTA/EtOH appear to be additive at 25° C. but not at 30° C. Since data from other experiments suggest that high polysorbate concentrations may be somewhat less beneficial to Ad5gag stability at ≧30° C. (see FIG. 20) the data generated at 25° C. may be a better predictor of the stability enhancement at 2-8° C. In summary, Ad5gag in a formulation containing the combination of EDTA/EtOH and 0.1% polysorbate (A136) was more stable than in formulations with either EDTA/EtOH (A113) or 0.1% polysorbate (A111) alone.

EXAMPLE 12

Additional Formulations Containing Free Radical Oxidation Inhibitors

The combination of EDTA and ethanol was found to greatly enhance the stability of Ad5gag, as shown in FIGS. 23 and 27. The data in FIG. 28 shows the effects of varying the concentration of ethanol and the effect of EDTA alone and ethanol alone, on the stability of adenovirus. The results indicate that the combination of 100 μM EDTA and 0.5% ethanol (in A113) provided the greatest enhancement of adenovirus stability after 2 months at 30° C., compared to adenovirus in A105. The results also showed that EDTA alone and ethanol alone each enhanced the stability of adenovirus. However, increasing the ethanol concentration from 0.5% to 1% (compare A132 to A134) did not provide any additional enhancement of adenovirus stability, at this temperature. The combination of high PS-80 (0.1%) and EDTA/Ethanol (in A136) provided approximately the same degree of stability enhancement as EDTA/Ethanol with 0.005% PS-80 (in A113), at 30° C. However, adenovirus was found to be more stable in A136 than in A113 at 25° C., see FIG. 27. In another formulation, A137, the addition of 1 mg/mL plasmid DNA was found to enhance the stability of adenovirus, compared to adenovirus in A105.

EXAMPLE 13

Long-Term Stability of Ad5gag in Selected Formulations

The long-term stability of Ad5gag in twelve different formulations is shown in FIG. 29. These data show the log loss of Ad5gag infectivity after 18 months in storage at 2-8° C. Based on these data the loss of Ad5gag infectivity in A105 was 0.33 logs/year, close to the estimate made in Example 10 above using the data from FIG. 23. These data clearly show that the addition of free radical oxidation inhibitors (in formulations A113, A114, A116-A121) enhance the stability of adenovirus during storage at 2-8° C. In this experiment the most stable formulations were A111, A113, A114, A117 and A120, which demonstrates the ability of EDTA/EtOH, DTPA, TEOA and mannitol to inhibit free radical oxidation and the stabilizing effects of higher concentrations of polysorbate 80 (0.1% in A111).

In another experiment the long-term stability of Ad5gag was evaluated in fifteen formulations after one year of storage at 2-8° C. The results, shown in FIG. 30, indicate that the most stable formulation was A136, which is similar to A113 except that the polysorbate 80 concentration is 0.1%. Ad5gag in A135 was also found to be more stable than in A105 and A113, suggesting that the optimal concentration of ethanol in A113 may be near 1%. However, because the variability of the QPA assay is ~0.15 logs it is not clear whether the other tested formulations are more stable than A05. These data also showed lower stability for Ad5gag in A111 compared to A105, a result that is inconsistent with the data in FIGS. 29 and 32.

In a third long-term study the stability of Ad5gag was examined after 9 months at 2-8° C. and 15° C. in eight formulations. The results, shown in FIG. 31, are consistent with those shown in FIGS. 27-29, and indicate that Ad5gag in A113 is more stable than in A105 at 2-8° C. and 15° C. The main purpose of this experiment was to determine whether a combination of free radical oxidation inhibitors would improve the stability of Ad5gag compared to Ad5gag in A113. The 15° C. stability data show that the most stable formulations in this experiment were A149, A151b, A152 and A153 and suggest that the combination of EDTA/EtOH with either mannitol (in A149), histidine (in A151b), histidine and TEOA (in A152) or histidine, TEOA, and glycerol (in A153) may enhance the stability of Ad5gag compared to A113. An examination of the Ad5gag infectivity at time zero indicated a decrease in infectivity for A149, suggesting that this formulation may not be completely stable to freeze/thaw cycles and that sucrose or some other sugar should be added to enhance its stability through freeze/thaw cycles. The data shown in FIG. 29 support this hypothesis since formulation A121 contains 5% sucrose in addition to 3% mannitol, and was stable through at least one freeze/thaw cycle from −70° C. to 2-8° C.

EXAMPLE 14

Stability of Leading Ad5gag Formulations Compared to Third Party Adenovirus Formulations Adenovirus formulations have recently been disclosed in PCT publication number WO 98/02522 (Transgene) and WO 99/41416 (Schering-Plough). To compare the stability of Ad5gag in the formulations of the present invention with these formulations, a stability study was conducted with Ad5gag in A105, A111, A113, A136, one formulation from WO 98/02522 (TG#2) and five formulations from WO 99/41416 (SP#1-SP#5), at $10^8$ vp/mL, as described below.
TG#2 10 mM Tris, 150 mM NaCl, 1 M Sucrose, 1 mM $MgCl_2$, 0.005% Polysorbate-80, pH 8.5;
SP#1 1.7 mg/ml Sodium Phosphate Monobasic Dihydrate, 1.7 mg/ml Tris, 0.4 mg/ml $MgCl_2$, 20 mg/ml Sucrose, 0.15 mg/ml PS-80, 100 mg/ml Glycerol, pH 7.53;
SP#2 1.7 mg/ml Sodium Phosphate Monobasic Dihydrate, 1.7 mg/ml Tris, 0.4 mg/ml $MgCl_2$, 20 mg/ml Sucrose, 0.15 mg/ml PS-80, 100 mg/ml Glycerol, pH 7.36;

SP#3 1.7 mg/ml Sodium Phosphate Monobasic Dihydrate, 1.7 mg/ml Tris, 0.4 mg/ml MgCl2, 20 mg/ml Sucrose, 100 mg/ml Glycerol, pH 7.6;

SP#4 1.7 mg/ml Sodium Phosphate Monobasic Dihydrate, 1.7 mg/ml Tris, 0.4 mg/ml MgCl2, 20 mg/ml Sucrose, 100 mg/ml Glycerol, pH 7.37;

SP#5 1.7 mg/ml Sodium Phosphate Monobasic Dihydrate, 1.7 mg/ml Tris, 0.4 mg/ml MgCl2, 20 mg/ml Sucrose, 5.8 mg/ml NaCl, 100 mg/ml Glycerol, pH 7.53.

FIG. 32 shows the data after 9 months of storage at 2-8° C. and 15° C. These results clearly indicate that Ad5gag was more stable in each of the formulations of the present invention than in TG#2 or in SP#1 or SP#2. Because data generated after one month of storage at 15° C. indicated that Ad5gag in SP#3, SP#4 and SP#5 lost more than one log of infectivity, these formulations were not examined at the 9 month timepoint. Consistent with the data in FIGS. 18-20 and 29, Ad5gag in A111 was more stable than in A105. Also consistent with the data shown in FIGS. 23, 27-29 and 31, Ad5gag was more stable in A113 than in A105.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A virus formulation comprising:
   a) a purified virus;
   b) a buffer;
   c) a sugar;
   d) a salt;
   e) a divalent cation;
   f) a non-ionic detergent; and,
   g) an EDTA/ethanol combination.

2. A virus formulation of claim 1 with a virus concentration in the range from about $1\times10^7$ vp/mL to about $1\times10^{13}$ vp/mL and a total osmolarity in a range from about 200 mOs/L to about 800 mOs/L.

3. A virus formulation of claim 1 with a virus concentration in the range from about $1\times10^7$ vp/mL to about $1\times10^{13}$ vp/mL, wherein the buffer is a Tris buffer, at a pH from about 7.0 to about 9.0.

4. A virus formulation of claim 3 wherein the sugar is sucrose at a weight to volume percentage from about 2% to about 7.5% and the salt is sodium chloride from about 25 mM to about 250 mM, such that the total osmolarity of the formulation is a range from about 200 mOs/L to about 800 mOs/L.

5. A virus formulation of claim 4 wherein the divalent cation is selected from the group consisting of $MgCl_2$ and $CaCl_2$ in an amount from about 0.1 mM to about 5 mM.

6. A virus formulation of claim 5 wherein the non-ionic detergent is selected from the group consisting of Polysorbate-80 and Polysorbate-40 at a concentration range from about 0.001% to about 2%.

7. A virus formulation of claim 1 further comprising histidine.

8. A virus formulation of claim 1 with a concentration in the range from about $1\times10^7$ vp/mL to about $1\times10^{13}$ vp/mL and a total osmolarity in a range from about 200 mOs/L to about 800 mOs/L wherein, said buffer is about 1 mM Tris to about 10 mM Tris to provide a pH range from about pH 7.5 to about pH 8.5;
said sugar is sucrose present in a weight to volume range of about 2% to about 8%;
said salt is NaCl present in a range from about 25 mM to about 250 mM;
said divalent cation is $MgCl_2$ in a range from about 0.1 mM to about 5 mM;
said surfactant is Polysorbate-80 at a concentration from about 0.001% to about 0.25%; and
said EDTA/ethanol combination is a combination of EDTA from about 1 μM to about 500 μM and ethanol from about 0.1% to about 5.0%; and
further comprising histidine from 5 mM to 10 mM.

9. A virus formulation of claim 8, wherein EDTA is at about 100 μM and ethanol is at about 0.5%.

10. A virus formulation of claim 2 comprising adenovirus and a formulation selected from the group consisting of formulation number A151b, A155, A159, A165, A167, A168, A169, A170, A171, A172 and A173.

11. An adenovirus formulation comprising a purified adenovirus and an EDTA/ethanol combination.

12. An adenovirus formulation of claim 11 further comprising a buffer, a sugar, a salt, a divalent cation, and a non-ionic detergent.

13. An adenovirus formulation of claim 12 with an adenovirus concentration in the range from about $1\times10^7$ vp/mL to about $1\times10^{13}$ vp/ml and a total osmolarity in a range from about 200 mOs/L to about 800 mOs/L.

14. An adenovirus formulation of claim 13, wherein the buffer is a Tris buffer, at a pH from about 7.0 to about 9.0.

15. An adenovirus formulation of claim 14 wherein the sugar is sucrose at a weight to volume percentage from about 2% to about 7.5% and the salt is sodium chloride from about 25 mM to about 250 mM.

16. An adenovirus formulation of claim 15 wherein the divalent cation is selected from the group consisting of $MgCl_2$ and $CaCl_2$ in an amount from about 0.1 mM to about 5 mM.

17. An adenovirus formulation of claim 16 wherein the non-ionic detergent is selected from the group consisting of Polysorbate-80 and Polysorbate-40 at a concentration range from about 0.001% to about 2%.

18. An adenovirus formulation of claim 11, comprising:
about 1 mM Tris to about 10 mM Tris to provide a pH range from about pH 7.5 to about pH 8.5;
sucrose in a weight to volume range of about 2% to about 8%;
NaCl in a range from about 25 mM to about 250 mM;
$MgCl_2$ in a range from about 0.1 mM to about 5 mM;
Polysorbate-80 at a concentration from about 0.001% to about 0.25%;
EDTA from about 1 μM to about 500 μM; and
ethanol from about 0.1% to about 5.0%.

19. An adenovirus formulation of claim 18, wherein EDTA is present from about 50 μM to about 250 μM, ethanol is present from about 0.25% to about 2.0% and further comprising histidine from 5 mM to 10 mM.

20. An adenovirus formulation of claim 12 further comprising histidine.

21. An adenovirus formulation of claim 12 wherein the sugar is sucrose at a weight to volume percentage from about 2% to about 7.5% and the salt is sodium chloride from about 25 mM to about 250 mM, such that the total osmolarity of the formulation is a range from about 200 mOs/L to about 800 mOs/L.

22. An adenovirus formulation of claim 21 wherein the divalent cation is selected from the group consisting of $MgCl_2$ and $CaCl_2$ in an amount from about 0.1 mM to about 5 mM.

23. An adenovirus formulation of claim 22 wherein the non-ionic detergent is selected from the group consisting of Polysorbate-80 and Polysorbate-40 at a concentration range from about 0.001% to about 2%.

24. An adenovirus formulation of claim 12 comprising adenovirus and a formulation selected from the group consisting of formulation number A151b, A155, A159, A165, A167, A168, A169, A170, A171, A172 and A173.

25. An adenovirus formulation of claim 20 wherein the sugar is sucrose at a weight to volume percentage from about 2% to about 7.5% and the salt is sodium chloride from about 25 mM to about 250 mM, such that the total osmolarity of the formulation is a range from about 200 mOs/L to about 800 mOs/L.

26. An adenovirus formulation of claim 25 wherein the divalent cation is selected from the group consisting of $MgCl_2$ and $CaCl_2$ in an amount from about 0.1 mM to about 5 mM.

27. An adenovirus formulation of claim 26 wherein the non-ionic detergent is selected from the group consisting of Polysorbate-80 and Polysorbate-40 at a concentration range from about 0.001% to about 2%.

28. An adenovirus formulation of claim 27 with an adenovirus concentration in the range from about $1 \times 10^7$ vp/mL to about $1 \times 10^{13}$ vp/mL, wherein the buffer is a Tris buffer, at a pH from about 7.0 to about 9.0.

29. An adenovirus formulation of claim 12, wherein
said purified adenovirus is present in a concentration in the range from about $1 \times 10^7$ vp/mL to about $1 \times 10^{13}$ vp/mL;
the total osmolarity in a range from about 200 mOs/L to about 800 mOs/L;
said buffer is about 1 mM Tris to about 10 mM Tris to provide a pH range from about pH 7.5 to about pH 8.5;
said sugar is sucrose present in a weight to volume range of about 2% to about 8%;
said salt is NaCl is present in a range from about 25 mM to about 250 mM;
said divalent cation is $MgCl_2$ in a range from about 0.1 mM to about 5 mM;
said surfactant is Polysorbate-80 at a concentration from about 0.001% to about 0.25%; and
said EDTA/ethanol combination is a combination of EDTA from about 1 µM to about 500 µM, ethanol from about 0.1% to about 5.0%; and,
said formulation further comprises histidine.

30. An adenovirus formulation of claim 29, wherein EDTA is at about 100 µM, ethanol is at about 0.5% and histidine is present from 5 mM to 10 mM.

31. An adenovirus formulation with an adenovirus concentration in the range from about $1 \times 10^7$ vp/mL to about $1 \times 10^{13}$ vp/mL and a total osmolarity in a range from about 200 mOs/L to about 800 mOs/L which comprises from about 5.0 mM to about 10 mM Tris at a pH from about 7.0 to about 9.0, sucrose at about 5% weight/volume, NaCl at about 75 mM, $MgCl_2$ from about 1 mM to 2 mM, Polysorbate-80 from about 0.005% to about 0.1% weight/volume, EDTA at about 100 µM, ethanol at about 0.5% weight/volume, and histidine from about 5 mM to about 10 mM.

32. An adenovirus formulation of claim 31 wherein the Tris buffer is present at about 10 mM, sucrose at about 5% weight/volume, NaCl at about 75 mM, $MgCl_2$ at about 1 mM, Polysorbate-80 from about 0.02% weight/volume, EDTA at about 100 µM, ethanol at about 0.5% weight/volume, and histidine at about 10 mM.

33. An adenovirus formulation comprising a recombinant adenovirus and an EDTA/ethanol combination.

34. An adenovirus formulation of claim 33 further comprising a buffer, a sugar, a salt, a divalent cation, and a non-ionic detergent.

35. An adenovirus formulation of claim 34 wherein the sugar is sucrose at a weight to volume percentage from about 2% to about 7.5% and the salt is sodium chloride from about 25 mM to about 250 mM, such that the total osmolarity of the formulation is a range from about 200 mOs/L to about 800 mOs/L.

36. An adenovirus formulation of claim 35 wherein the divalent cation is selected from the group consisting of $MgCl_2$ and $CaCl_2$ in an amount from about 0.1 mM to about 5 mM and the non-ionic detergent is selected from the group consisting of Polysorbate-80 and Polysorbate-40 at a concentration range from about 0.001% to about 2%.

37. An adenovirus formulation of claim 34, comprising:
about 1 mM Tris to about 10 mM Tris to provide a pH range from about pH 7.5 to about pH 8.5;
sucrose in a weight to volume range of about 2% to about 8%;
NaCl in a range from about 25 mM to about 250 mM;
$MgCl_2$ in a range from about 0.1 mM to about 5 mM;
Polysorbate-80 at a concentration from about 0.001% to about 0.25%;
EDTA from about 1 µM to about 500 µM; and
ethanol from about 0.1% to about 5.0%.

\* \* \* \* \*